(12) United States Patent
Fukunaga

(10) Patent No.: US 9,173,878 B2
(45) Date of Patent: Nov. 3, 2015

(54) BRAIN FUNCTION IMPROVING AGENT

(71) Applicant: Tohoku University, Miyagi (JP)

(72) Inventor: Kohji Fukunaga, Miyagi (JP)

(73) Assignee: Tohoku University, Miyagi (JP)

( * ) Notice: Subject to any disclaimer, the term of this patent is extended or adjusted under 35 U.S.C. 154(b) by 0 days.

(21) Appl. No.: 14/374,354

(22) PCT Filed: Jan. 24, 2013

(86) PCT No.: PCT/JP2013/051388
§ 371 (c)(1),
(2) Date: Jul. 24, 2014

(87) PCT Pub. No.: WO2013/111799
PCT Pub. Date: Aug. 1, 2013

(65) Prior Publication Data
US 2015/0045385 A1 Feb. 12, 2015

(30) Foreign Application Priority Data

Jan. 25, 2012 (JP) .................................. 2012/012897

(51) Int. Cl.
C07D 471/04 (2006.01)
A61K 31/437 (2006.01)
A61K 31/4545 (2006.01)
C07D 471/10 (2006.01)
A61K 31/438 (2006.01)

(52) U.S. Cl.
CPC ........... *A61K 31/4545* (2013.01); *A61K 31/437* (2013.01); *A61K 31/438* (2013.01); *C07D 471/10* (2013.01)

(58) Field of Classification Search
USPC .......................................... 546/121; 514/300
See application file for complete search history.

(56) References Cited

U.S. PATENT DOCUMENTS

2004/0048879 A1    3/2004    Kawashima et al.

FOREIGN PATENT DOCUMENTS

WO    WO 02/060907 A1    8/2002
WO    WO 03/080046 A1    10/2003

OTHER PUBLICATIONS

Abe et al., "Synthesis of Spiro[2-cyclopentene-1,3'-imidazo[1,2-α]-pyridine] derivatives and their interesting behavior in $^1$H-NMR spectra in deuteriochloroform," Heterocycles, 2010, 81(9):2075-2088.

Han et al., "Spiro[imidazo[1,2-α]pyridine-3,2-indan]-2(3H)-one (ZSET1446/ST101) Treatment Rescues Olfactory Bulbectomy-Induced Memory Impairment by Activating $Ca^{2+}$/Calmodulin Kinse II and Protein Kinase C in Mouse Hippocampus," 2008, 326(1):127-134.

Moriguchi et al., "Nefiracetam activation of CaM kinase II and protein kinase C mediated by NMDA and and metabotropic glutamate receptors in olfactory bulbectomized mice," Journal of Neurochemistry, 2009, 110:170-181.

Moriguchi et al., "The T-type voltage-gated calcium channel as a molecular target of the novel cognitive enhancer ST101: enhancement of long-term potentiation and CaMKII autophosphorylation in rat cortical slices," Journal of Neurochemistry, 2012, 10.1111/j.1471-4159.2012.07667.x, 10 pages.

Shioda et al., "Neurochemical Mechanisms of a Novel Alzheimer's Disease Therapeutics on Improvement of Cognition and Depressive Behavior," Journal of the Pharmaceutical Society of Japan, 2011, 131(4):505-511, English abstract on first page.

Yamaguchi et al., "Effects of a Novel Cognitive Enhancer, Spiro[imidazo-[1,2-α]pyridine-3,2-indan]-2(3H)-one (ZSET1446), on Learning Impairments Induced by Amyloid-$\beta_{1-40}$ in the Rat," Journal of Pharmacology and Experimental Therapeutics, 2006, 317(6):1079-1087.

*Primary Examiner* — Nyeemah A Grazier
(74) *Attorney, Agent, or Firm* — Foley & Lardner LLP

(57) ABSTRACT

The present invention provides a pharmaceutical composition used in improving brain function including a compound of formula (I).

12 Claims, 15 Drawing Sheets

BRAIN FUNCTION IMPROVING AGENT

CROSS-REFERENCE TO RELATED APPLICATIONS

This application is a National Stage application of PCT/JP2013/051388, filed Jan. 24, 2013, which claims priority from Japanese application JP 2012-012897, filed Jan. 25, 2012.

TECHNICAL FIELD

The present invention relates to a pharmaceutical agent that is useful in improving the brain function and a method for improving the brain function using such agent, particularly a therapeutic method or a preventive method for cognitive dysfunction. Further, the present invention relates to a screening method of an agent that is useful in improving the brain function.

BACKGROUND ART

Diseases relating to brain function, such as Alzheimer's disease, are becoming a worldwide problem, and Japan, which is fast becoming an aging society, must urgently solve the issue of overcoming those diseases. There are said to be about 20,000,000 patients of Alzheimer type cognitive disorder in the world, and in Japan, 40% or more of the about 1,500,000 cognitive disorder patients are presumed to have Alzheimer type cognitive disorder.

Donepezil hydrochloride (Aricept (Registered Trademark)), which is an cholinesterase inhibitor, is used widely as a powerful means of treating Alzheimer's disease, and a new acetyl cholinesterase inhibitor is approved for production. However, the efficacy ratio of the clinical result of donepezil hydrochloride is about 50%, and a stronger and safer agent is awaited.

Exploration and research for a new pharmaceutical agent aimed at improving brain function by a new action mechanism is also under way. For example, ZSET1446 having an acetylcholine liberator effect and nefiracetam having a N-methyl-D-aspartate (NMDA) receptor activating effect have been reported, and clinical tests have been performed (Patent Documents 1 and 2, Non-Patent Documents 1 to 4). However, there is currently no new pharmaceutical agent approved for production other than acetyl cholinesterase inhibitor, and a strong desire exists for development of a new pharmaceutical agent having an action mechanism differing from existing pharmaceutical agents.

Further, the main accessory symptom for high-level brain dysfunctions including mental disease (schizophrenia, bipolar disorder, depression, phobia, sleep disorder, drug dependence, etc.), pervasive developmental disorder (autism, Asperger's syndrome, mental deficiency, polyergic disorder, tic disorder, etc.) is cognitive dysfunction. The prognosis of the disease is known to improve by a remedial teaching-based cognitive function improvement method, but development of an effective cognitive function improving agent is strongly awaited.

CITATION LIST

Patent Documents

Patent Document 1: International Publication WO 2003/080046

Patent Document 2: International Publication WO 2002/060907

Non-Patent Documents

Non-Patent Document 1: The Journal of Pharmacology and Experimental Therapeutics Vol. 326, No. 1, 127-134, 2008;

Non-Patent Document 2: The Journal of Pharmacology and Experimental Therapeutics Vol. 317, No. 3, 1079-1087, 2006;

Non-Patent Document 3: Yakugaku Zasshi Vol. 130, No. 5, 717-721, 2010;

Non-Patent Document 4: Journal of Neurochemistry Vol. 110, 170-181, 2009;

SUMMARY OF INVENTION

Technical Problem

The present invention aims to provide a new pharmaceutical agent that is useful for improving brain function, and to provide a method for improving brain function using such agent. The present invention further aims to provide a screening method of a pharmaceutical agent that is useful for improving brain function.

Solution to Problem

The present inventors conducted an extensive study to achieve the above object and found that a group of compound having a heterospiro ring structure has a brain function improving effect, and thus completed the present invention.

An aspect of the present invention provides a pharmaceutical composition of (1) to (7) below.

(1) A pharmaceutical composition used for improving brain function comprising a compound represented by formula (I):

[Formula 1]

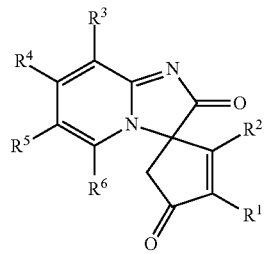

(I)

wherein, $R^1$ is a hydrogen atom, $C_{1-6}$ alkyl, cyano, —C(=O)$NR^{11}R^{12}$, or —C(=O)$OR^{13}$;

$R^2$ is a hydrogen atom, $C_{1-6}$ alkyl, hydroxy, —$X^1$—$R^{14}$, or —$NR^{15}R^{16}$;

$R^3$, $R^4$, $R^5$, and $R^6$ are each independently selected from a hydrogen atom, a halogen atom, $C_{1-6}$ alkyl, hydroxy, $C_{1-6}$ alkoxy, $C_{1-6}$ alkylthio, $C_{1-6}$ alkylsulfinyl, $C_{1-6}$ alkylsulfonyl, amino, $C_{1-6}$ alkylamino, di($C_{1-6}$ alkyl)amino, cyano, nitro, —C(=O)$NR^{17}R^{18}$, and —C(=O)$OR^{19}$;

$R^{11}$ and $R^{12}$ are each independently selected from a hydrogen atom, $C_{1-6}$ alkyl, $C_{6-10}$ aryl, and 5- to 10-membered heteroaryl; or $R^{11}$ and $R^{12}$, together with a nitrogen atom to which they are attached, form a nitrogen-containing heterocycle, and the nitrogen-containing heterocycle may be substituted with one or more substituents selected from $C_{1-6}$ alkyl, hydroxy, hydroxy$C_{1-6}$ alkyl, $C_{1-6}$ alkoxy, $C_{1-6}$ alkoxy$C_{1-6}$ alkyl, $C_{1-6}$ alkylthio, $C_{1-6}$ alkylsulfinyl, $C_{1-6}$ alkylsulfonyl, amino, $C_{1-6}$ alkylamino, di($C_{1-6}$ alkyl)amino, amino $C_{1-6}$ alkyl, ($C_{1-6}$ alkylamino)$C_{1-6}$ alkyl, [di($C_{1-6}$ alkyl)amino]$C_{1-6}$ alkyl, —C(=O)NR$^{22}$R$^{23}$, —C(=O)OR$^{24}$, —($C_{1-6}$ alkyl)C(=O)NR$^{22}$R$^{23}$, and —($C_{1-6}$ alkyl)C(=O)OR$^{24}$;

$R^{13}$ is selected from a hydrogen atom, $C_{1-6}$ alkyl, $C_{6-10}$ aryl, and 5- to 10-membered heteroaryl, wherein the alkyl group may be substituted with one or more substituents selected from $C_{6-10}$ aryl, hydroxy, $C_{1-6}$ alkoxy, $C_{1-6}$ alkylthio, $C_{1-6}$ alkylsulfinyl, $C_{1-6}$ alkylsulfonyl, amino, $C_{1-6}$ alkylamino, di($C_{1-6}$ alkyl)amino, —C(=O)NR$^{22}$R$^{23}$, and —C(=O)OR$^{24}$;

$X^1$ is —O—, —S—, —SO—, or —SO$_2$—;

$R^{14}$ is selected from $C_{1-6}$ alkyl, $C_{6-10}$ aryl, and 5- to 10-membered heteroaryl;

$R^{15}$ is hydrogen atom, $C_{1-6}$ alkyl, $C_{6-10}$ aryl, 5- to 10-membered heteroaryl, or —C(=O)—R$^{21}$, wherein the alkyl group may be substituted with one or more substituents selected from $C_{6-10}$ aryl, hydroxy, $C_{1-6}$ alkoxy, $C_{1-6}$ alkylthio, $C_{1-6}$ alkylsulfinyl, $C_{1-6}$ alkylsulfonyl, amino, $C_{1-6}$ alkylamino, di($C_{1-6}$ alkyl)amino, —C(=O)NR$^{22}$R$^{23}$, and —C(=O)OR$^{24}$;

$R^{16}$ is a hydrogen atom, $C_{1-6}$ alkyl, $C_{6-10}$ aryl, or 5- to 10-membered heteroaryl, wherein the alkyl group may be substituted with one or more substituents selected from $C_{6-10}$ aryl, hydroxy, $C_{1-6}$ alkoxy, $C_{1-6}$ alkylthio, $C_{1-6}$ alkylsulfinyl, $C_{1-6}$ alkylsulfonyl, amino, $C_{1-6}$ alkylamino, di($C_{1-6}$ alkyl) amino, —C(=O)NR$^{22}$R$^{23}$, and —C(=O)OR$^{24}$; or $R^{15}$ and $R^{16}$, together with a nitrogen atom to which they are attached, form a nitrogen-containing heterocycle group, and the nitrogen-containing heterocycle group may be substituted with one or more substituents selected from $C_{1-6}$ alkyl, hydroxy, hydroxyl $C_{1-6}$ alkyl, $C_{1-6}$ alkoxy, $C_{1-6}$ alkoxy$C_{1-6}$ alkyl, $C_{1-6}$ alkylthio, $C_{1-6}$ alkylsulfinyl, $C_{1-6}$ alkylsulfonyl, amino, $C_{1-6}$ alkylamino, di($C_{1-6}$ alkyl)amino, amino$C_{1-6}$ alkyl, ($C_{1-6}$ alkylamino)$C_{1-6}$ alkyl, [di($C_{1-6}$ alkyl) amino]$C_{1-6}$ alkyl, —C(=O)NR$^{22}$R$^{23}$, —C(=O)OR$^{24}$, —($C_{1-6}$ alkyl)C(=O)NR$^{22}$R$^{23}$, and —($C_{1-6}$ alkyl)C(=O) OR$^{24}$;

$R^{17}$ and $R^{18}$ are each independently selected from a hydrogen atom, $C_{1-6}$ alkyl, $C_{6-10}$ aryl, and 5- to 10-membered heteroaryl; or $R^{17}$ and $R^{18}$, together with a nitrogen atom to which they are attached, form a nitrogen-containing heterocycle;

$R^{19}$ is selected from a hydrogen atom, $C_{1-6}$ alkyl, $C_{6-10}$ aryl, and 5- to 10-membered heteroaryl;

$R^{21}$ is selected from a hydrogen atom, $C_{1-6}$ alkyl, $C_{1-6}$ alkoxy, $C_{6-10}$ aryl, and 5- to 10-membered heteroaryl, wherein the alkyl group and the alkoxy group may be substituted with one or more substituents selected from $C_{6-10}$ aryl, hydroxy, $C_{1-6}$ alkoxy, $C_{1-6}$ alkylthio, $C_{1-6}$ alkylsulfinyl, $C_{1-6}$ alkylsulfonyl, amino, $C_{1-6}$ alkylamino, di($C_{1-6}$ alkyl)amino, —C(=O)NR$^{22}$R$^{23}$, and —C(=O)OR$^{24}$;

$R^{22}$ and $R^{23}$ are each independently selected from a hydrogen atom, $C_{1-6}$ alkyl, $C_{6-10}$ aryl, and 5- to 10-membered heteroaryl, or $R^{22}$ and $R^{23}$, together with a nitrogen atom to which they are attached, form a nitrogen-containing heterocycle group;

$R^{24}$ is each independently selected from hydrogen atom, $C_{1-6}$ alkyl, $C_{6-10}$ aryl, and 5- to 10-membered heteroaryl, or a pharmaceutically acceptable salt thereof.

(2) The composition according to (1), wherein $R^1$ is —C(=O)OR$^{13}$, and $R^{13}$ is $C_{1-6}$ alkyl that may be substituted with one or more substituents defined in (1).

(3) The composition according to (1) or (2), wherein $R^2$ is $C_{1-6}$ alkylthio or —NR$^{15}$R$^{16}$, and $R^{15}$ and $R^{16}$ are as defined in (1).

(4) The composition according to (3), wherein group-NR$^{15}$R$^{16}$ is $C_{1-6}$ alkylamino, di($C_{1-6}$ alkyl)amino, [($C_{1-6}$ alkoxycarbonyl)$C_{1-6}$ alkyl]amino, or [($C_{6-10}$ aryl)$C_{1-6}$ alkyl] amino, or group —NR$^{15}$R$^{16}$ is a nitrogen-containing heterocyclic group selected from a 1-pyrrolidinyl, 1-piperidinyl, 1-piperazinyl, 4-morpholinyl, or 1-homopiperidinyl, wherein the nitrogen-containing heterocyclic group may be substituted with one or more substituents defined in (1).

(5) The composition according to (1) to (4), wherein $R^3$, $R^4$, $R^5$, and $R^6$ are each independently selected from a hydrogen atom, and $C_{1-6}$ alkyl.

(6) A composition according to any one of (1) to (5), wherein the compound represented by formula (I) or a pharmaceutically acceptable salt thereof is selected from:

2',3'-dihydro-2-methylthio-2',4-dioxospiro[2-cyclopenten-1,3'-imidazo-[1,2-a]pyridin]-3-carboxylic acid ethyl ester;

2',3'-dihydro-8-methyl-2-methylthio-2',4-dioxospiro[2-cyclopenten-1,3'-imidazo[1,2-a]pyridin]-3-carboxylic acid ethyl ester;

2',3'-dihydro-6,8-dimethyl-2-methylthio-2',4-dioxospiro[2-cyclopenten-1,3'-imidazo[1,2-a]pyridin]-3-carboxylic acid ethyl ester;

2',3'-dihydro-2-methylamino-2',4-dioxospiro[2-cyclopenten-1,3'-imidazo-[1,2-a]pyridin]-3-carboxylic acid ethyl ester;

2',3'-dihydro-8-methyl-2-methylamino-2',4-dioxospiro[2-cyclopenten-1,3'-imidazo[1,2-a]pyridin]-3-carboxylic acid ethyl ester;

2',3'-dihydro-6,8-dimethyl-2-methylamino-2',4-dioxospiro[2-cyclopenten-1,3'-imidazo[1,2-a]pyridin]-3-carboxylic acid ethyl ester;

2',3'-dihydro-2',4-dioxo-2-(phenethylamino)spiro[2-cyclopenten-1,3'-imidazo-[1,2-a]pyridin]-3-carboxylic acid ethyl ester;

2',3'-dihydro-8-methyl-2',4-dioxo-2-(phenethylamino) spiro[2-cyclopenten-1,3'-imidazo[1,2-a]pyridin]-3-carboxylic acid ethyl ester;

2',3'-dihydro-6,8-dimethyl-2',4-dioxo-2-(phenethylamino)spiro[2-cyclopenten-1,3'-imidazo[1,2-a]pyridin]-3-carboxylic acid ethyl ester;

2',3'-dihydro-2-(ethoxycarbonylmethyl)amino-2',4-dioxospiro[2-cyclopenten-1,3'-imidazo[1,2-a]pyridin]-3-carboxylic acid ethyl ester;

2',3'-dihydro-2-(ethoxycarbonylmethyl)amino-8-methyl-2',4-dioxospiro[2-cyclopenten-1,3'-imidazo[1,2-a]pyridin]-3-carboxylic acid ethyl ester;

2',3'-dihydro-2-(ethoxycarbonylmethyl)amino-6,8-dimethyl-2',4-dioxospiro[2-cyclopenten-1,3'-imidazo[1,2-a]pyridin]-3-carboxylic acid ethyl ester;

2',3'-dihydro-2-dimethylamino-2',4-dioxospiro[2-cyclopenten-1,3'-imidazo[1,2-a]pyridin]-3-carboxylic acid ethyl ester;

2',3'-dihydro-2-dimethylamino-8-methyl-2',4-dioxospiro [2-cyclopenten-1,3'-imidazo[1,2-a]pyridin]-3-carboxylic acid ethyl ester;

2',3'-dihydro-2-dimethylamino-6,8-dimethyl-2',4-dioxospiro[2-cyclopenten-1,3'-imidazo[1,2-a]pyridin]-3-carboxylic acid ethyl ester;

2',3'-dihydro-2',4-dioxo-2-piperidinospiro[2-cyclopenten-1,3'-imidazo[1,2-a]pyridin]-3-carboxylic acid ethyl ester;

2',3'-dihydro-8-methyl-2',4-dioxo-2-piperidinospiro[2-cyclopenten-1,3'-imidazo[1,2-a]pyridin]-3-carboxylic acid ethyl ester;

2',3'-dihydro-6,8-dimethyl-2',4-dioxo-2-piperidinospiro[2-cyclopenten-1,3'-imidazo[1,2-a]pyridin]-3-carboxylic acid ethyl ester.

(7) The composition according to any one of (1) to (6), for use in a treatment or prevention of cognitive dysfunction.

(8) The composition according to (7), wherein the cognitive dysfunction is a disease selected from neurodegenerative disease, mental disease, and pervasive developmental disorder.

(9) The composition according to (7), wherein the cognitive dysfunction is a disease selected from Alzheimer's disease, Parkinson disease, Pick's disease, and Huntington's disease, schizophrenia, bipolar disorder, depression, phobia, sleep disorder, drug dependence, autism, Asperger's syndrome, mental deficiency, polyergic disorder, and tic disorder.

Another aspect of the present invention provides the method for improving brain function described in (10) to (15) below.

(10) A method for improving brain function comprising administering an effective amount of a compound represented by formula (I):

[Formula 2]

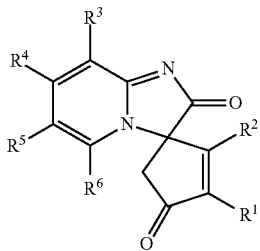

(I)

wherein, $R^1$, $R^2$, $R^3$, $R^4$, $R^5$, and $R^6$ are as defined in (1).

(11) The method according to (10), wherein $R^1$ is $-C(=O)OR^{13}$, and $R^{13}$ is a $C_{1-6}$ alkyl that may be substituted with one or more substituents defined in (1).

(12) The method according to (10) or (11), wherein $R^2$ is $C_{1-6}$ alkylthio or $-NR^{15}R^{16}$, and $R^{15}$ and $R^{16}$ are as defined in (1).

(13) The method according to (12), wherein group $-NR^{15}R^{16}$ is $C_{1-6}$ alkylamino, di($C_{1-6}$ alkyl)amino, [($C_{1-6}$ alkoxycarbonyl)$C_{1-6}$ alkyl]amino, or [($C_{6-10}$ aryl)$C_{1-6}$ alkyl]amino, or group $-NR^{15}R^{16}$ is a nitrogen-containing heterocyclic group selected from 1-pyrrolidinyl, 1-piperidinyl, 1-piperazinyl, 4-morpholinyl, or 1-homopiperidinyl, wherein the nitrogen-containing heterocyclic group may be substituted with one or more substituents defined in (1).

(14) The method according to any one of (10) to (13), wherein $R^3$, $R^4$, $R^5$, and $R^6$ is each independently selected from a hydrogen atom, and $C_{1-6}$ alkyl.

(15) The method according to any one of (10) to (14), wherein the compound represented by formula (I) or a pharmaceutically acceptable salt thereof is selected from compounds recited in (6) and pharmaceutically acceptable salts thereof.

A further aspect of the present invention provides a therapeutic method or a preventive method according to (16) to (21) below.

(16) A therapeutic method or preventive method for cognitive dysfunction comprising administering an effective amount of a compound represented by formula (I) to a subject:

[Formula 3]

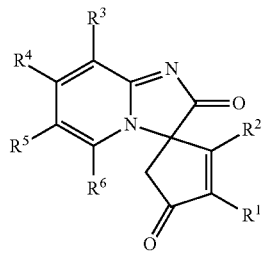

(I)

wherein, $R^1$, $R^2$, $R^3$, $R^4$, $R^5$, and $R^6$ are as defined in (1).

(17) The method according to (16), wherein $R^1$ is $-C(=O)OR^{13}$, and $R^{13}$ is a $C_{1-6}$ alkyl that may be substituted with one or more substituents defined in (1).

(18) The method according to (16) or (17), wherein $R^2$ is $C_{1-6}$ alkylthio or $-NR^{15}R^{16}$, and $R^{15}$ and $R^{16}$ are as defined in (1).

(19) The method according to (18), wherein group $-NR^{15}R^{16}$ is $C_{1-6}$ alkylamino, di($C_{1-6}$ alkyl)amino, [($C_{1-6}$ alkoxycarbonyl)$C_{1-6}$ alkyl]amino, or [($C_{6-10}$ aryl)$C_{1-6}$ alkyl]amino, or group $-NR^{15}R^{16}$ is a nitrogen-containing heterocyclic group selected from 1-pyrrolidinyl, 1-piperidinyl, 1-piperazinyl, 4-morpholinyl, or 1-homopiperidinyl, wherein the nitrogen-containing heterocyclic group may be substituted with one or more substituents defined in (1).

(20) The method according to any one of (16) to (19), wherein $R^3$, $R^4$, $R^5$, and $R^6$ is each independently selected from a hydrogen atom, and $C_{1-6}$ alkyl.

(21) The method according to any one of (16) to (20), wherein the compound represented by formula (I) or a pharmaceutically acceptable salt thereof is selected from compounds recited in (6) and pharmaceutically acceptable salts thereof.

A further aspect of the present invention provides a screening method according to (22) to (31) below.

(22) A method for screening a compound having an activity of improving brain function comprising a step of selecting a compound that is effective in increasing the amount of influent alcium ion of the voltage-dependent t-type calcium channel.

(23) The method according to (22), wherein the voltage-dependent t-type calcium channel is selected from Cav 3.1, Cav 3.2, and Cav 3.3.

(24) The method according to (22) or (23) comprising a step of adding a test compound to a test system using a voltage-dependent t-type calcium channel-expressing cell, and measuring the change in the level of intracellular calcium ion by the addition.

(25) The method according to any one of (22) to (24), using a voltage-dependent t-type calcium channel-expressing cell from transfecting a voltage-dependent t-type calcium channel gene to the cell.

(26) The method according to (25), wherein the voltage-dependent t-type calcium channel gene is transfected to a cell selected from Neuro2A cell, PC12 cell, HEK293 cell, and COS7 cell.

(27) A screening method of a compound having an activity to improve brain function, comprising:
(a) a step of preparing 2 types of nerve cells having different expression amounts for a voltage-dependent t-type calcium channel;
(b) a step of adding the test compound to an assay system (Assay System A) using cells with a low expression amount of the voltage-dependent t-type calcium channel (Cell A), and measuring the change in the level of intracellular calcium ion by the addition;
(c) a step of adding the test compound to an assay system (Assay System B) using cells with a high expression amount of the voltage-dependent t-type calcium channel (Cell B), and measuring the change in the level of intracellular calcium ion by the addition;
(d) a step of selecting a compound having a higher increase in the calcium level of Assay B than the increase in Assay A.
(28) The method of (27), wherein Cell B is a voltage-dependent t-type calcium channel gene-transfected cell.
(29) The method according to (27) or (28), further comprising a step of confirming that the intracellular calcium level increases by nicotin addition for both Assay Systems A and B.
(30) The method according to (27) to (29), wherein Cell A is a cell selected from Neuro2A cell, PC12 cell, HEK293 cell, and COS7 cell.
(31) The method according to (27) to (30), wherein Cell B is Cell A having a Cav 3.1, Cav 3.2, or Cav 3.3 gene transfected therein.

A different aspect of the present invention provides a voltage-dependent t-type calcium channel activator according to (32) to (37) below.

(32) A voltage-dependent t-type calcium channel activator comprising an effective amount of a compound represented by formula (I):

[Formula 4]

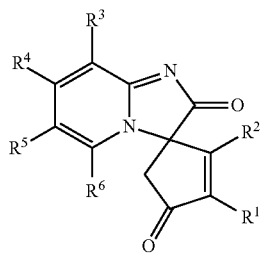

(I)

wherein. $R^1$, $R^2$, $R^3$, $R^4$, $R^5$, and $R^6$ are as defined in (1).

(33) The voltage-dependent t-type calcium channel activator according to (32), wherein $R^1$ is —C(=O)$OR^{13}$, and $R^{13}$ is a $C_{1-6}$ alkyl that may be substituted with one or more substituents defined in (1).

(34) The voltage-dependent t-type calcium channel activator according to (32) or (33), wherein $R^2$ is $C_{1-6}$ alkylthio or —$NR^{15}R^{16}$, and $R^{15}$ and $R^{16}$ are as defined in (1).

(35) The voltage-dependent t-type calcium channel activator according to (34), wherein group —$NR^{15}R^{16}$ is $C_{1-6}$ alkylamino, di($C_{1-6}$ alkyl)amino, [($C_{1-6}$ alkoxycarbonyl)$C_{1-6}$ alkyl]amino, or [($C_{6-10}$ aryl)$C_{1-6}$ alkyl]amino, or group —$NR^{15}R^{16}$ is a nitrogen-containing heterocyclic group selected from 1-pyrrolidinyl, 1-piperidinyl, 1-piperazinyl, 4-morpholinyl, or 1-homopiperidinyl, wherein the nitrogen-containing heterocyclic group may be substituted with one or more substituents defined in (1).

(36) The voltage-dependent t-type calcium channel activator according to any one of (32) to (35), wherein $R^3$, $R^4$, $R^5$, and $R^6$ is each independently selected from a hydrogen atom, and $C_{1-6}$ alkyl.

(37) The voltage-dependent t-type calcium channel activator according to any one of (32) to (36), wherein the compound represented by formula (I) or a pharmaceutically acceptable salt thereof is selected from compounds recited in (6) and pharmaceutically acceptable salts thereof.

Advantageous Effects of Invention

The present invention provides a new pharmaceutical composition that may be used for improving brain function, particularly a therapeutic agent or a preventive agent that constitutes a method for treating cognitive dysfunction, such as Alzheimer's disease. Further, the present invention provides an efficient screening method of a compound that is useful for improving brain function.

DESCRIPTION OF EMBODIMENTS

Figure 1:
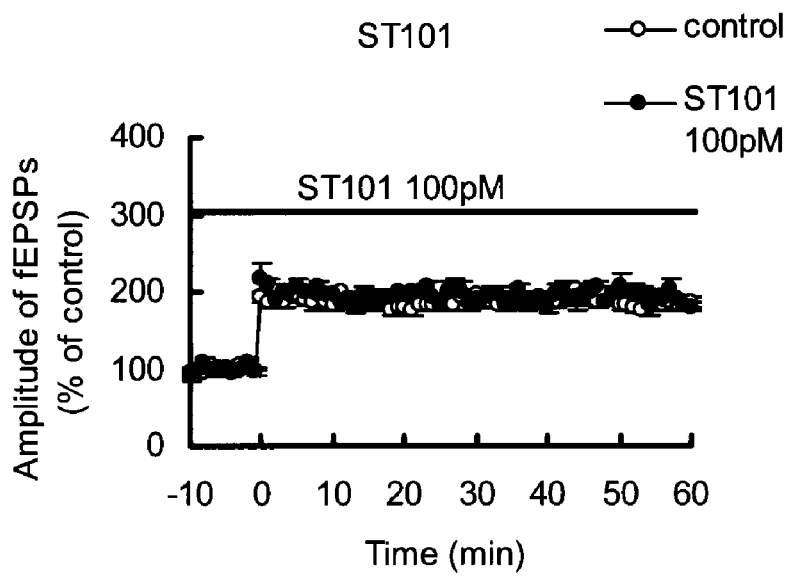
FIG. 1 is a chart showing the effect of ST101 (100 pM) in long-term potentiation of synaptic transmission in hippocampus. The horizontal axis shows the amplitude of postsynaptic potential (fEPSP; field excitatory postsynaptic potential0081), and the vertical axis shows the elapsed time.
Figure 2:
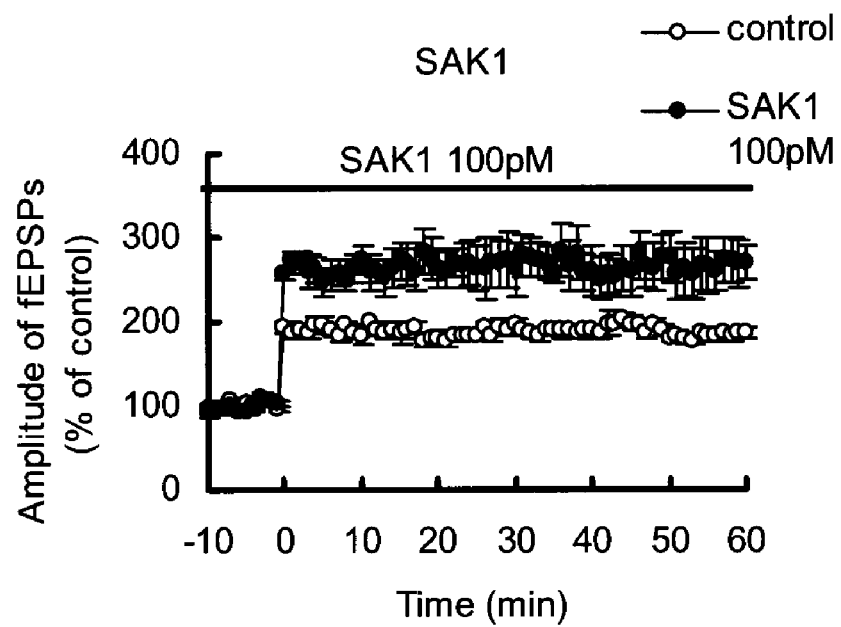
FIG. 2 is a chart showing the effect of SAK1 (100 pM) in long-term potentiation of synaptic transmission in hippocampus. The horizontal axis shows the amplitude of postsynaptic potential (fEPSP; field excitatory postsynaptic potential), and the vertical axis shows the elapsed time.
Figure 3:
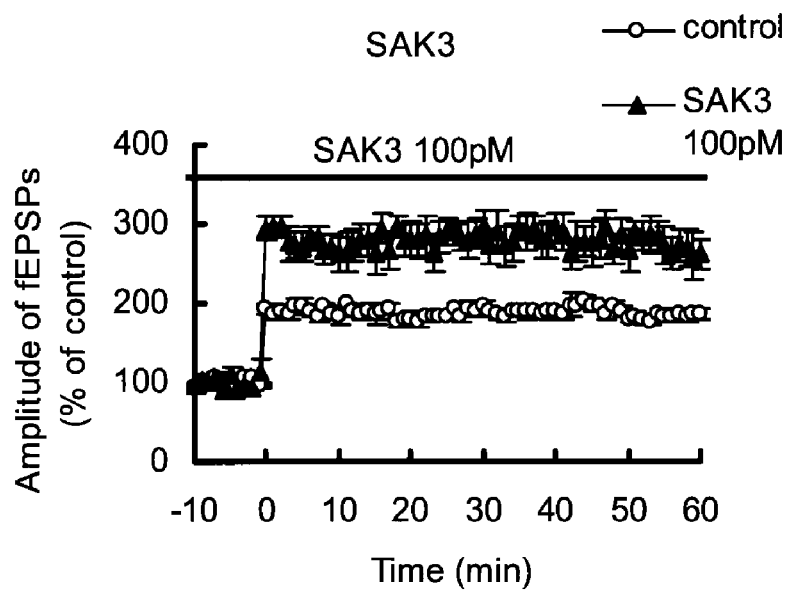
FIG. 3 is a chart showing the effect of SAK3 (100 pM) in long-term potentiation of synaptic transmission in hippocampus. The horizontal axis shows the amplitude of postsynaptic potential (fEPSP; field excitatory postsynaptic potential), and the vertical axis shows the elapsed time.
Figure 4:
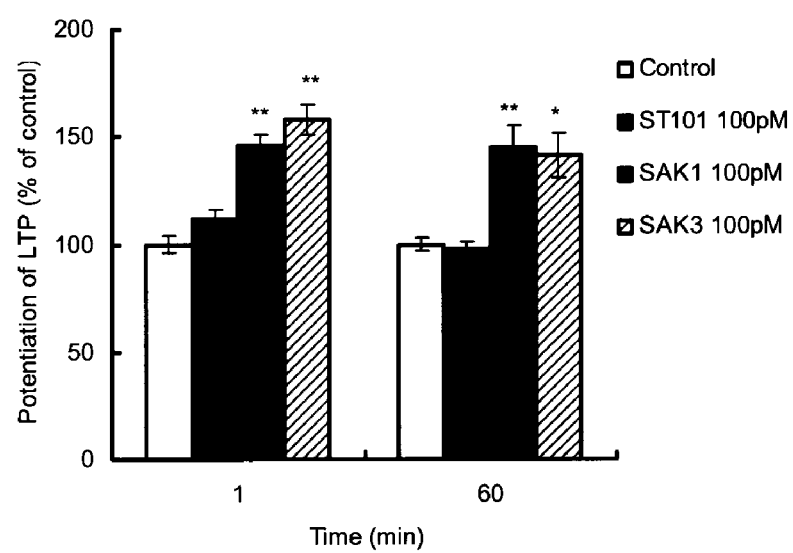
FIG. 4 is a graph showing the LTP strength at 1 minute and 60 minutes after administration of ST101, SAK1 and SAK3 to each administration group. The * ($p<0.05$), ** ($p<0.01$) in the drawing show the significance between the control and the group of test compounds.

The present invention is explained in more detail below.

According to an aspect of the present invention, a pharmaceutical composition comprising a compound represented by the above formula (I) or pharmaceutically acceptable salt, particularly a pharmaceutical composition used in improving brain function, a brain function improving agent, or a therapeutic agent or a preventive agent for cognitive dysfunction.

Concerning the definition of formula (I), "$C_{1-6}$ alkyl" is a straight chain, branched, cyclic or partially cyclic alkyl group of 1 to 6 carbons, and includes methyl, ethyl, n-propyl, i-propyl, n-butyl, s-butyl, i-butyl, t-butyl, n-pentyl, 3-methylbutyl, 2-methylbutyl, 1-methylbutyl, 1-ethylpropyl, n-hexyl, 4-methylpentyl, 3-methylpentyl, 2-methylpentyl, 1-methylpentyl, 3-ethylbutyl, and 2-ethylbutyl, cylcopropyl, cylcobutyl, cylcopentyl, cylcohexyl, and cylcopropylmethyl, and it also includes $C_{1-4}$ alkyl and $C_{1-3}$ alkyl.

In the present specification, "$C_{1-6}$ alkoxy" is an alkyloxy group [—O—($C_{1-6}$ alkyl)] having the predefined alkyl group of 1 to 6 carbons as the alkyl part, and includes methoxy, ethoxy, n-propoxy, i-propoxy, n-butoxy, s-butoxy, i-butoxy, t-butoxy, n-pentoxy, 3-methylbutoxy, 2-methylbutoxy, 1-methylbutoxy, 1-ethylpropoxy, n-hexyloxy, 4-methylpentoxy, 3-methylpentoxy, 2-methylpentoxy, 1-methylpentoxy, 3-ethylbutoxy, cylcopentyloxy, cylcohexyloxy, and cylcopropylmethyloxy, and it also includes $C_{1-4}$ alkoxy and $C_{1-3}$ alkoxy. Further, "$C_{1-4}$ alkoxy" in the present specification also includes $C_{1-3}$ alkoxy.

In the present specification, "$C_{1-6}$ alkylthio" is an alkylthio group [—S—($C_{1-6}$ alkyl)] having the predefined alkyl group of 1 to 6 carbons as the alkyl part, and includes methylthio, ethylthio, n-propylthio, i-propylthio, n-butylthio, s-butylthio, i-butylthio, t-butylthio, n-pentylthio, 3-methylbutylthio, 2-methylbutylthio, 1-methylbutylthio, 1-ethylpropylthio, n-hexylthio, 4-methylpentylthio, 3-methylpentylthio, 2-methylpentylthio, 1-methylpentylthio, 3-ethylbutylthio, 2-ethylbutylthio, cylcopropylthio, cylcobutylthio, cylcopentylthio, cylcohexylthio, and cylcopropylmethylthio, and it also includes $C_{1-4}$ alkylthio and $C_{1-3}$ alkylthio.

In the present specification, "$C_{1-6}$ alkylsulfinyl" is an alkylsulfinyl group [—SO—($C_{1-6}$ alkyl)] having the predefined alkyl group of 1 to 6 carbons as the alkyl part, and includes methylsulfinyl, ethylsulfinyl, n-propylsulfinyl, i-propylsulfinyl, n-butylsulfinyl, s-butylsulfinyl, i-butylsulfinyl, t-butylsulfinyl, n-pentylsulfinyl, 3-methylbutylsulfinyl, 2-methylbutylsulfinyl, 1-methylbutylsulfinyl, 1-ethylpropylsulfinyl, n-hexylsulfinyl, 4-methylpentylsulfinyl, 3-methylpentylsulfinyl, 2-methylpentylsulfinyl, 1-methylpentylsulfinyl, 3-ethylbutylsulfinyl, 2-ethylbutylsulfinyl, cylcopropylsulfinyl, cylcobutylsulfinyl, cylcopentylsulfinyl, cylcohexylsulfinyl, and cylcopropylmethylsulfinyl, and it also includes $C_{1-4}$ alkylsulfinyl and $C_{1-3}$ alkylsulfinyl.

In the present specification, "$C_{1-6}$ alkylsulfonyl" is an alkylsulfonyl group [—SO$_2$—($C_{1-6}$ alkyl)] having the predefined alkyl group of 1 to 6 carbons as the alkyl part, and includes methylsulfonyl, ethylsulfonyl, n-propylsulfonyl, i-propylsulfonyl, n-butylsulfonyl, s-butylsulfonyl, i-butylsulfonyl, t-butylsulfonyl, n-pentylsulfonyl, 3-methylbutylsulfonyl, 2-methylbutylsulfonyl, 1-methylbutylsulfonyl, 1-ethylpropylsulfonyl, n-hexylsulfonyl, 4-methylpentylsulfonyl, 3-methylpentylsulfonyl, 2-methylpentylsulfonyl, 1-methylpentylsulfonyl, 3-ethylbutylsulfonyl, 2-ethylbutylsulfonyl, cylcopropylsulfonyl, cylcobutylsulfonyl, cylcopentylsulfonyl, cylcohexylsulfonyl, and cylcopropylmethylsulfonyl, and it also includes $C_{1-4}$ alkylsulfonyl and $C_{1-3}$ alkylsulfonyl.

In the present specification, "$C_{1-6}$ alkylamino" is an alkylamino group [—NH—($C_{1-6}$ alkyl)] having the predefined alkyl group of 1 to 6 carbons as the alkyl part, and includes methylamino, ethylamino, n-propylamino, i-propylamino, n-butylamino, s-butylamino, i-butylamino, t-butylamino, n-pentylamino, 3-methylbutylamino, 2-methylbutylamino, 1-methylbutylamino, 1-ethylpropylamino, n-hexylamino, 4-methylpentylamino, 3-methylpentylamino, 2-methylpentylamino, 1-methylpentylamino, 3-ethylbutylamino, 2-ethylbutylamino, cylcopropylamino, cylcobutylamino, cylcopentylamino, cylcohexylamino, and cylcopropylmethylamino, and it also includes $C_{1-4}$ alkylamino and $C_{1-3}$ alkylamino.

In the present specification, "di($C_{1-6}$ alkyl)amino" is a dialkylamino group [—NH—($C_{1-6}$ alkyl)$_2$] having the predefined alkyl group of 1 to 6 carbons as the two alkyl parts, and the two alkyl parts may be the same or different. Examples of the group include dimethylamino, diethylamino, di(n-propyl)amino, di(i-propyl)amino, di(n-butyl)amino, di(s-butyl)amino, di(i-butyl)amino, di(t-butyl)amino, di(n-pentyl)amino, di(3-methylbutyl)amino, di(2-methylbutyl)amino, di(1-methylbutyl)amino, di(1-ethylpropyl)amino, di(n-hexyl)amino, di(4-methylpentyl)amino, di(3-methylpentyl)amino, di(2-methylpentyl)amino, di(1-methylpentyl)amino, di(3-ethylbutyl)amino, di(2-ethylbutyl)amino, dicylcopropylamino, dicylcobutylamino, dicylcopentylamino, dicylcohexylamino, and dicylcopropylmethylamino, and ethyl(methyl)amino, n-propyl(methyl)amino, i-propyl(methyl)amino, n-butyl(methyl)amino, s-butyl(methyl)amino, i-butyl(methyl)amino, t-butyl(methyl)amino, n-pentyl(methyl)amino, (3-methylbutyl)(methyl)amino, (2-methylbutyl)(methyl)amino, (1-methylbutyl)(methyl)amino, (1-ethylpropyl)(methyl)amino, n-hexyl(methyl)amino, (4-methylpentyl)(methyl)amino, (3-methylpentyl)(methyl)amino, (2-methylpentyl)(methyl)amino, (1-methylpentyl)(methyl)amino, (3-ethylbutyl)(methyl)amino, and (2-ethylbutyl)(methyl)amino, cylcopropyl(methyl)amino, cylcobutyl(methyl)amino, cylcopentyl(methyl)amino, cylcohexyl(methyl)amino, and (cylcopropylmethyl)(methyl)amino, and it also includes ($C_{1-4}$ alkyl)(methyl)amino and ($C_{1-3}$ alkyl)(methyl)amino.

In the present specification, "$C_{1-6}$ alkoxycarbonyl" is an alkoxycarbonyl group having the predefined $C_{1-6}$ alkoxy group as the alkyl part, and includes methoxycarbonyl, ethoxycarbonyl, tert-butoxycarbonyl, as well as $C_{1-3}$ alkoxycarbonyl.

In the present specification, "hydroxyl $C_{1-6}$ alkyl" includes hydroxymethyl, 2-hydroxyethyl, 1-hydroxyethyl.

In the present specification, "amino $C_{1-6}$ alkyl" includes aminomethyl, 2-aminoethyl, 1-aminoethyl.

In the present specification, "$C_{1-6}$ alkoxy $C_{1-6}$ alkyl" is a group represented by the formula —($C_{1-6}$ alkyl)-O—($C_{1-6}$ alkyl), and includes methoxymethyl, ethoxymethyl, 2-methoxyethyl, 1-methoxyethyl.

In the present specification, "$C_{1-6}$ alkylamino $C_{1-6}$ alkyl" is a group represented by the formula —($C_{1-6}$ alkyl)-NH—($C_{1-6}$ alkyl), and includes (methylamino)methyl, (ethylamino)methyl, 2-(methylamino)ethyl, 1-(methylamino)ethyl.

In the present specification, "di($C_{1-6}$ alkylamino)$C_{1-6}$ alkyl" is a group represented by the formula —($C_{1-6}$ alkyl)-N($C_{1-6}$ alkyl)$_2$, and the two alkyl group of the dialkylamino part may be the same or different. Examples of the group includes (dimethylamino)methyl, (diethylamino)methyl, 2-(dimethylamino)ethyl, 1-(dimethylamino)ethyl.

In the present specification, "—($C_{1-6}$ alkyl)C(=O)NR$^{22}$R$^{23}$" is a group in which any carbon atom of $C_{1-6}$ alkyl is substituted with a group —C(=O)NR$^{22}$R$^{23}$, and $C_{1-6}$ alkyl is as predefined.

In the present specification, "—($C_{1-6}$ alkyl)C(=O)OR$^{24}$" is a group in which any carbon atom of $C_{1-6}$ alkyl is substituted with a group —C(=O)OR$^{24}$, and $C_{1-6}$ alkyl is as predefined.

In the present specification, "$C_{6-10}$ aryl" is, for example, phenyl, 1-naphthyl or 2-naphthyl.

In the present specification, a "5- to 10-membered heteroaryl" is an aromatic heterocyclic group that is a monocycle or a fused ring consisting of 5 to 10 atoms containing one or more hetero atoms selected from an oxygen atom, nitrogen atom and a sulfur atom. Specific examples include pyrrolyl, imidazolyl, pyrazolyl, triazolyl, pyridyl, pyrimidyl, pyridazinyl, furyl, thienyl, oxazolyl, oxadiazolyl, thiazolyl, thiadiazolyl, indolyl, quinolinyl, quinoxalyl, quinazolinyl, benzothiophenyl, benzofuranyl.

In the present specification, a "nitrogen-containing heterocyclic group" is a saturated, partially-saturated or non-saturated heterocyclic group that is a monocycle or a fused ring consisting of 5 to 10 atoms containing one nitrogen atom and also optionally containing one or more hetero atoms selected from an oxygen atom, nitrogen atom and a sulfur atom. Specific examples include pyrrolyl, imidazolyl, pyrazolyl, triazolyl, tetrazolyl, indolyl, pyrrolidinyl, piperidinyl, piperazinyl, homopiperidinyl, morpholinyl.

The present invention relating to a compound represented by the above formula (I) includes various stereoisomers, such as a tautomer, a geometrical isomer, an enantiomer, and mixtures thereof. For example, the compound represented by formula (I) encompasses the compounds of formula (Ia) and (Ib) below.

[Formula 5]

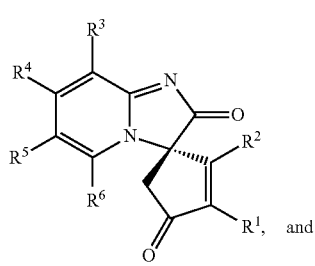

(Ia) and

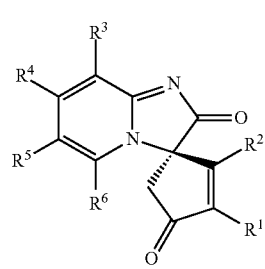

(Ib)

A "pharmaceutically acceptable salt" of a compound of formula (I) is not particularly limited as long as it is a salt that may be used as a pharmaceutical product. The salt formed from the compound of the present invention in combination with a base may be a salt formed with an inorganic base, such as sodium, potassium, magnesium, calcium, aluminum, etc.; or a salt with an organic base, such as methylamine, ethylamine, ethanolamine, etc. The salt may also be an acid addition salt, which may be an acid addition salt with a mineral acid, such as hydrochloric acid, hydrobromic acid, hydriodic acid, sulfuric acid, nitric acid, and phosphoric acid; or a salt with an organic acid, such as formic acid, acetic acid, propionic acid, oxalic acid, malonic acid, succinic acid, fumaric acid, maleic acid, lactic acid, malic acid, tartaric acid, citric acid, methansulfonic acid, ethansulfonic acid.

Further, the compound represented by formula (I) also includes a hydrate, various solvates or crystalline polymorphs.

Each of the atom (e.g. a hydrogen atom, a carbon atom, an oxygen atom, a nitrogen atom, and a sulfur atom) contained in the compound represented by formula (I) may be an isotopic atom of an isotope other than that constituting the largest number in nature, and the isotopic atom may be a radioisotopic atom. In other words, an aspect of the present invention provides a compound of formula (I) defined in the present specification, labeled by an isotopic atom, or a salt thereof. Labeling by an isotopic atom may be performed as labeling using a radioisotope ($^3$H, $^{14}$C, $^{32}$P, etc.), and labeling should preferably be performed using $^3$H in view of the ease of preparing the compound.

In an aspect of the present invention, the compound of formula (I) is administered as a prodrug, and converted to an active compound in the living body.

The compound of formula (I) may be prepared, for example, by the production method described in Heterocycles, Vol. 81, No. 9, 2010, 2075-2086. To provide an example, the compound of formula (I) can be synthesized by a process shown by the following scheme.

Scheme A

[Formula 6]

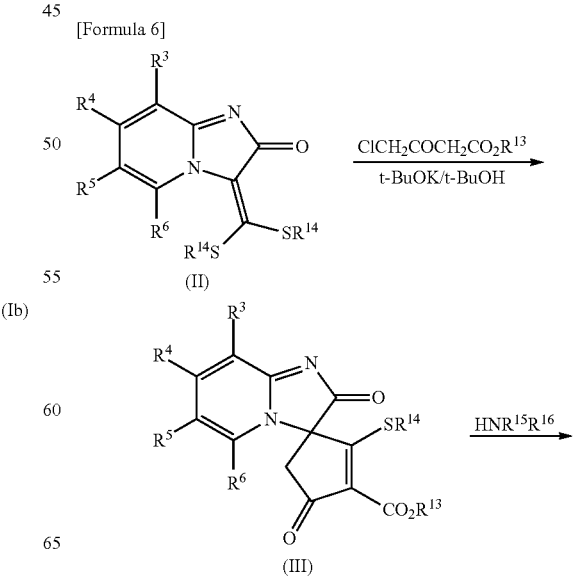

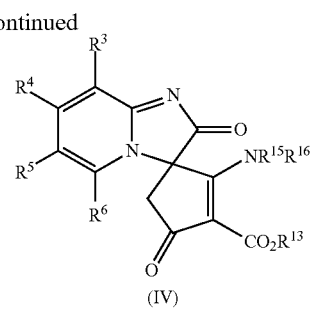

(IV)

wherein, $R^3$, $R^4$, $R^5$, $R^6$, $R^{13}$, $R^{14}$, $R^{15}$, and $R^{16}$ are as previously defined in the present specification.

The compound of formula (II) can be converted to a compound of formula (III) by being reacted with chloroacetoacetic ester (e.g. chloroacetoacetic ethyl ester) in a solvent such as chloroform under the presence of base, and under room temperature. The compound of formula (III) can be converted to a compound of formula (IV) by reaction with amine in a solvent of a suitable solvent (e.g. chloroform) under superheat (e.g. under reflux of a solvent). The desired compound of formula (I) may be synthesized by using a compound of formula (II) corresponding to the desired compound, or by converting the substituent of a compound of formula (III) or formula (IV). A protective group may be inserted or eliminated as necessary.

The improving of the brain function in the present invention includes improving brain dysfunctions, for example, brain dysfunctions caused by cerebrovascular disease, brain damage, brain tumor, viral encephalitis, hypoxic encephalopathy, and alcoholism. The present invention may be applied particularly to cognitive dysfunctions, such as dysmnesia, attentional deficit, executive function deficit, social behavior disorder. Cognitive dysfunctions include, for example, neurodegenerative disease (Alzheimer's disease, Parkinson disease, Pick's disease, and Huntington's disease, etc.), mental disease (schizophrenia, bipolar disorder, depression, phobia, sleep disorder, drug dependence, etc.), and pervasive developmental disorder (autism, Asperger's syndrome, mental deficiency, polyergic disorder, tic disorder, etc.).

The pharmaceutical composition of the present invention may be of various dosage forms without being limited thereby, including tablet, capsule, powder, granule, pill, liquid formulation, emulsion, suspension, solution agent, spirit, syrup, extract, elixir for oral administration; and injections, such as hypodermic injection, intravenous injection, intramuscular injection, intraperitoneal injection, dermal administration or patches, ointments or lotion for parenteral agents; and sublingual agents, or intraoral patches for intraoral administration; and aerosol agents for nasal administration. These pharmaceutical preparations can be produced by a publicly known method commonly used in the preparation process.

The pharmaceutical composition may include various components used generally, and it may include at least one of a pharmaceutically acceptable excipient, disintegrator, diluent, lubricant, fragrance, coloring agent, sweetener, corrective, suspending agent, wetting agent, emulsifying agent, disperser, adjuvant, antiseptic, buffer, binder, stabilizer, coating agent. Further, the pharmaceutical composition of the present invention may be a prolonged dosage form or sustained-release dosage form.

The administration amount of the therapeutic agent, preventive agent or pharmaceutical composition of the present invention may be selected as necessary according to the administration route, the body type, age, condition of the patient, level of disease, and the elapsed time after the onset. The pharmaceutical composition of the present invention may include the compound of formula (I) at a therapeutic effective dose and/or preventive effective dose. The compound of formula (I) may be generally used in a dosage of 1 to 10000 mg/day/adult. The administration of the pharmaceutical composition may be a single administration or multiple administrations.

The therapeutic agent or preventive agent of the present invention may include components, such as a coloring agent, stabilizer, fragrance, flavoring agent, coating agent, antioxidant, vitamin, amino acid, peptide, protein, and minerals (iron, zinc, magnesium, iodine). The therapeutic agent or preventive agent may be prepared in the form suitable for a pharmaceutical composition, a functional food, a health food, drinks and supplements, including forms of various solid pharmaceutical formulations such as granules (including dry syrop), capsules (soft capsules, hard capsules), tablets (including chewable agents), powders (epistasic), pills, or liquid pharmaceutical formulations such as a liquid formulation for internal use (including a liquid formulation, suspending agent, and syrups). Further, the therapeutic agent or preventive agent of the present invention may be used as-is as a pharmaceutical composition, functional food, health food, and supplement.

An additive for a pharmaceutical formulation includes an excipient, lubricant, binder, disintegrator, fluidization agent, disperser, wetting agent, antiseptic, viscous agent, pH adjuster, coloring agent, corrector, surfactant, solubilizer. Further, a thickener, such as a pectin, xanthan gum, guar gum, may be added. Further, a coating tablet or a paste-like leim may be formed using a coating agent. Further, even when preparing the formulation in other forms, a conventional method may be followed.

An aspect of the present invention provides a screening method of a compound having a brain function improving activity comprising a step of selecting a compound having an effect of increasing the amount of influent calcium ion in the voltage-dependent t-type calcium channel. In the above step, the compound may be selected by an assay using a voltage-dependent t-type calcium channel expression cell.

Another aspect of the present invention provides a screening method of a compound having a brain function improving activity using 2 types of nerve cells having different expression amounts for a voltage-dependent t-type calcium channel. The test compound which is a screening object is not particularly limited, and examples include an organic compound and an inorganic compound (particularly, a low molecular compound), protein and peptide.

The voltage-dependent t-type calcium channel expression cell used in screening is not particularly limited. A nerve cell whose calcium ion level shows a significant increase by the addition of a compound represented by the following formula (SAK3)

[Formula 7]

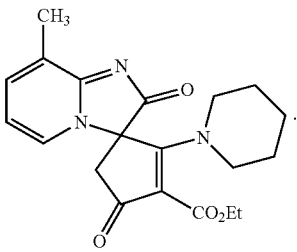

The two types of nerve cells having a different expression amount for voltage-dependent t-type calcium channel are not particularly limited as long as the expression amount differ significantly. Preferably, a nerve cell in which the level of calcium ion does not substantially increase by the addition of a compound represented by the above formula (SAK3) may be used as a cell (Cell A) having a low expression amount of the voltage-dependent t-type calcium channel. Further, a nerve cell exhibiting a significant increase in the calcium ion level by the addition of the above compound may be preferably used as a cell (Cell B) having a high expression amount for voltage-dependent t-type calcium channel.

The screening of the present invention may use cells derived from mammals, specifically, it can use cells derived from human, or cells derived from non-human mammals, such as a mouse, rat, rabbit, dog, cat or monkey.

The screening of the present invention may use a natural cell having a low expression amount of voltage-dependent t-type calcium channel, which specifically includes neuroblastoma cells (e.g. Neuro2A cells, PC12 cells), HEK293 cells, COS7 cells. Or else, a knock out cell of a voltage-dependent t-type calcium channel gene may be used. These cells can be used as cell A.

Specific examples of voltage-dependent t-type calcium channel expression cells include central nervous cells (e.g. hippocampus cone cell, thalamic sense related cell, cerebellum purkinje cells, olfactory bulb granular cells), and peripheral motor nerve cell (e.g. dorsal spinal sensory nerve, adrenomedullary cell). Further, a voltage-dependent t-type calcium channel-transfected gene recombination cell incorporating can be used. Examples of voltage-dependent t-type calcium channels, in which genes are transfected, are Cav 3.1, Cav 3.2, Cav 3.3. These cells can be used as cell B. Specific examples of cells in which a gene is transfected include neuroblastoma cells (e.g. Neuro2A cells, PC12 cells), HEK293 cells, COS7 cells.

The assay system in the screening method of the present invention, particularly in both assay system A using cell A and assay system B using cell B, may include a step to confirm the increase of the calcium ion level by adding nicotin. By this step, the presence of a $Ca^{2+}$ influent path other than a voltage-dependent t-type calcium channel can be confirmed in both assay systems, and the present screening method can be validated.

Cultivation of a cell and a preparation of gene recombination cell can be performed by a publicly known method. Further, an administration of a test compound can be performed by incorporating a test compound in a solution holding the cell and inducing the test compound to act against the target.

The screening method of the present invention may be used in the screening of a compound having the effect of promoting acetylcholine liberation by an increase in the amount of influen $Ca^{2+}$ in a voltage-dependent t-type calcium channel. Such compounds possess a brain function improving effect resulting from the promotion of acetylcholine liberation, and it has a similar feature as a compound subjected to a clinical test, such as ZSET1446, and a preferable feature as a medicine in view of the risk of side effects.

A further aspect of the present invention provides a voltage-dependent t-type calcium channel activator comprising a compound of formula (I). The compound of formula (I) is as previously defined in the present specification. The voltage-dependent t-type calcium channel activator of the present invention can be used, for examples, as a reagent for tests. Another aspect of the present invention provides a method for activating a voltage-dependent t-type calcium channel comprising a step of adding a compound of formula (I) to a system including a voltage-dependent t-type calcium channel.

EXAMPLES

The present invention is described in more detail by showing the Examples, without being limited thereby.

Reagents and Statistic Treatment

The following reagent was used in a test:

[Formula 8]

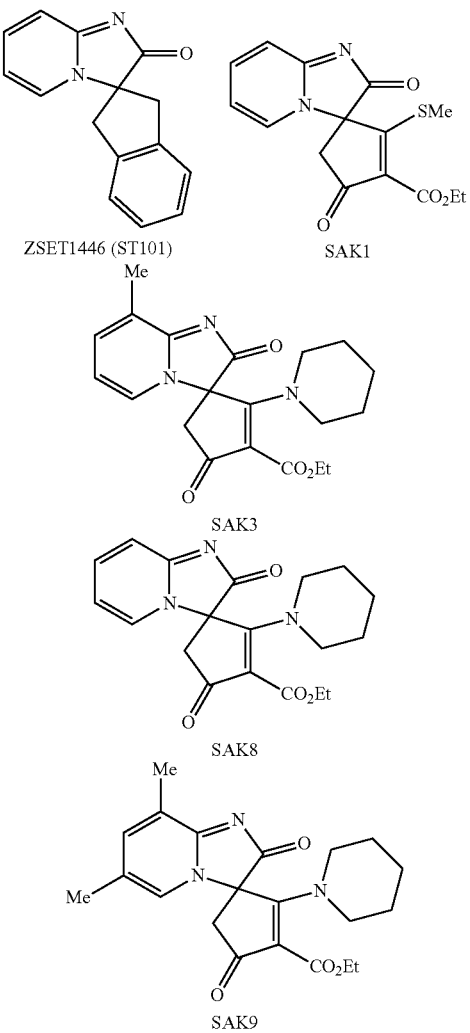

ZSET1446 (hereinafter referred to as ST101) can be synthesized by a publicly known method. A compound provided by Sonexa Therapeutics Inc (San Diego, USA) was used in the present test. SAK derivative which is a compound of formula (I) can be prepared by the method in Heterocycles, Vol. 81, No. 9, 2010, 2075-2086. A compound provided by Professor Akikazu Kakehi of the National University Corporation Shinshu University was used in the present test. Mibefradil dihydrocholoride was purchased from Sigma-Aldrich.

All data was calculated by the average value±standard error. Concerning the significant statistic difference, the comparison between multiple groups was performed by using a one-way analysis of variance followed by a multiple comparison method of Dunnett. Further, a risk rate of less than 5% was the criteria to judge that there was a statistically significant difference.

Test Example 1

Effect of Long-Term Potentiation of Synaptic Transmission (LTP) in the Mouse Hippocampus CA1 Region The brain of a male mouse C57BL/6 (10-12 weeks old) was sagitally sectioned, then a coronal section brain slice (400 μm) including a hippocampus CA1 region was prepared. The hippocampus slice was recovered in an artificial cerebrospinal fluid (126 mM NaCl, 5 mM KCl, 26 mM $NaHCO_3$, 1.3 mM $MgSO_4$-$7H_2O$, 1.26 mM $KH_2PO_4$, 2.4 mM $CaCl_2$-$2H_2O$, 10 mM glucose) saturated by a 95% $O_2$/5% $CO_2$ gas at 34° C. for 2 hours. The hippocampus slice was transferred to a measurement chamber, and ST101 (100 pM), SAK1 (100 pM), SAK3 (100 pM) were added to the artificial cerebrospinal fluid, and perfused. Then, the Schaffer branch to be input to the hippocampus CA1 region and the commissural fibers were stimulated by stimulus electrodes, and the postsynaptic potential (fEPSP; field excitatory postsynaptic potential) in the CA1 region induced thereby was measured. After measurement, just the hippocampus CA1 region was sliced from the slice segment, and frozen for preservation at −80° C. for measurement with immunoblotting.

The results are shown in FIGS. 1 to 4. The long-term potentiation of synaptic transmission (LTP) in hippocampus is an elementary process of memory in mammals. ST101 does not show a strong LTP potentiation effect during a clinical test, but a strong potentiation effect was observed in SAK1 and SAK3. It can be expected from the present experiment result that the brain function improving agent of the present invention induces a long-term potentiation of synaptic transmission of the present invention to improve the brain function concerning memory.

Test Example 2

Effect of CaMKII in the Hippocampus CA1 Region on the Self-Phosphorylation Reaction (Activation Reaction)

The above frozen mouse brain slice segment (hippocampus CA1 region) is used for homogenization on ice by adding 150 μL homogenizing buffer (50 mM Tris-HCl pH 7.5, 0.5% Triton X-100, 4 mM EGTA, 0.5 M NaCl, 10 mM EDTA, 1 mM $Na_3VO_4$, 30 mM sodium pyrophosphate, 50 mM NaF, 1 mM DTT, 100 nM calyculin A, 50 μg/mL leupeptin, 25 μg/mL pepstatin A, 50 μg/mL trypsin inhibitor) per sample. Then, centrifugation was performed using a refrigerated centrifuge (14,000×g, 10 minutes, 4° C.), after which 100 μL of supernatant was collected and 20 μL of 6× Laemmli buffer was added to the supernatant to be boiled at 100° C. for 3 minutes, to form an immunoblotting sample. The protein concentration was measured by the Bradford method using a part of the supernatant. Reagants containing the same amount of protein were added to 10% SDS-polyacrylamido electrophoresis gel (SDS-PAGE gel), and SDS-PAGE was performed at 80 mA per 1 sheet of gel for 180 minutes. After separation by electrophoresis, transcription to a PVDF membrane was performed at 70 V for 120 minutes. The membrane was immersed in Tween, Tris-bufferd saline (TTBS:50 mM Tris-HCl, pH 7.5, 150 mM NaCl and 0.1% Tween 20) that dissolves skim milk at a 5% concentration to prevent non-specific bonding of an antibody, and blocked at a normal temperature for 1 hour, then the following first antibody was reacted at 4° C. overnight. An antiphosphorylation CaMKII antibody (1:5000, Fukunaga et al., J. Biol. Chem. 267, 22527-22533, 1992) and an antiphosphorylation CaMKII antibody (1:5000, Fukunaga et al., J. Neurochem. 51, 1070-1078, 1988) were used as the first antibody. After washing with a TTBS solution, the membrane was reacted with a second antibody of horseradish peroxidase (HRP)-labeled anti-rabbit IgG antibody (1:5000, GE healthcare, Buckinghamshire, UK) at a normal temperature for 60 minutes. After washing with a TTBS solution, ECL detection system (GE healthcare) was used to induce luminescence of HRP that labels the second antibody, and the X-ray film (Fuji Medical X-ray Film, Fuji Film) was sensitized to detect the band. An NIH image analysis software was used for a quantification analysis of the immunoreaction product.

Figure 5:
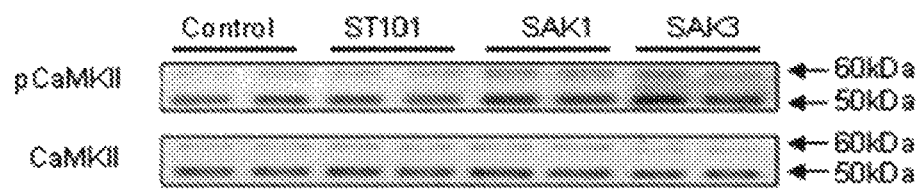
FIG. 5 is a chart showing the result of blotting using an anti-phosphorylating CaMKII antibody and an anti-CaMKII antibody, in which the self-phosphorlyation of CaMKII by the immunoblot is compared between the control and the group of test compounds (ST101, SAK1 and SAK3) after treatment by extracting the hippocampus CA1 region 60 minutes after LTP.
Figure 6:
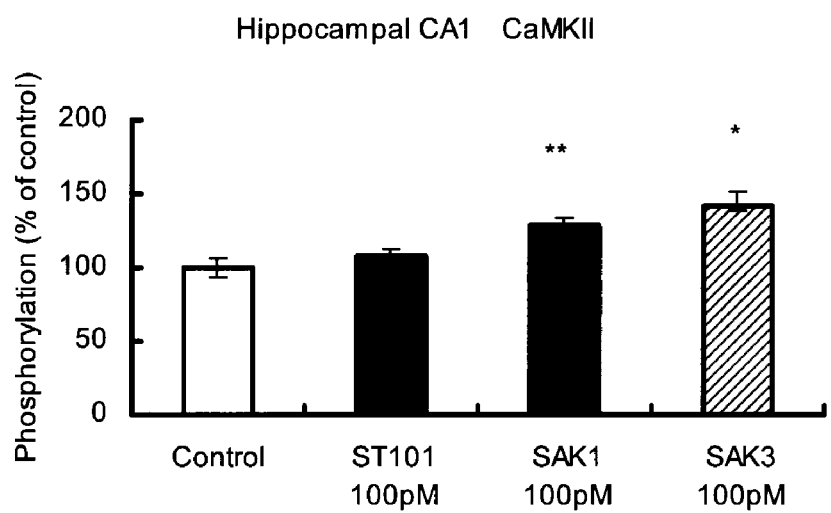
FIG. 6 is a graph showing the self-phosphorylation of CaMKII in the hippocampus CA1 region of a mouse based on the quantitative analysis result of the immunoreaction product from blotting. The horizontal axis of the graph is the calculated value of the stimulating effect of the test compound against the self phosphorylation of the control. The * ($p<0.05$), ** ($p<0.01$) in the drawing show the significance between the control and the group of test compounds treatment.

The result of blotting using an anti-phosphorylation CaMKII antibody and an anti CaMKII antibody was shown in FIG. 5, and the result of a quantification result of an immunoreactions product is shown in the graph of FIG. 6. The activation (self-phosphorylation) of a calcium/calmodulin dependent protein kinase II (CaMKII) that is essential for the long-term potentiation of synaptic transmission (LTP) in a hippocampus is essential. In a mouse that was administered SAK1 and SAK3 having an LTP potentiation effect, an increase of phosphorylated CaMKII and a potentiation of CaMKII activation were confirmed.

Test Example 3

Effects in T-Type Calcium Channel Non-Expressing Cells and Expressing Cells

The cells of mouse neuroblastoma cell line Neuro2A were purchased from the Human Science Research Resources Bank (#IFO50081, Osaka, Japan). The Neuro2A cells were cultivated in a Dulbecco's modified eagle medium (DMEM) including a 10% fetal bovine serum under the condition of 37° C./5% $CO_2$. Then, the Neuro2A cells were seeded to a glass bottom dish at a concentration of 1 to 2×$10^6$ cell/φ35-mm dish, and cultivated for 24 hours in a standard culture medium, and the cells were transfected using Lipofectamine 2000 (Invitrogen, Carsbad, Calif., USA) and using a plasmid vector containing a T-type calcium channel (Cav 3.1) genes (serum-free culture of Lipofectamine 2000: DNA=1 μl: 1 μg, 1.5 ml). The T-type calcium channel (Cav 3.1) gene, the plasmid vector pCMV-SPORT6, and the Lipofectamine 2000 were respectively purchased from OriGene Technologies, Inc., Thermo Fisher Scientific Ltd., and Invitrogen, and the transfection was performed according to the protocol attached to Lipofectamine 2000 other than the rate adjustment of the Lipofectamine 2000 and plasmid vector. The serum-free culture was replaced with a standard culture 6 hours after transfect, and calcium imaging (calcium concentration measurement) was performed after Cav 3.1 expression was confirmed after 48 hours of culture.

T-type calcium channel expressing Neuor2A cells were dispersed in a glass bottom dish, and 2.5 μM of Fura-2-AM (Sigma, St Louis, Mo., USA) was added to the dish in perfusion (Krebs-Hepes buffer; KRH), then the dish was incubated at 37° C. for 30 minutes. A Fura-2-AM-free KRH was replaced with perfusion, and the Neuro2A cells were stimulized with SAK3 (100 pM) as the intracellular calcium was measured with a fluorescent microscope, then the cells were further stimulized with nicotin (1 μM), ATP (0.1 μM), DHPG (20 μM), as necessary. In a system for adding mibefradil (10

μM), which is a T type calcium channel inhibitor, the cells were added to the reflux (external solution).

Figure 7:
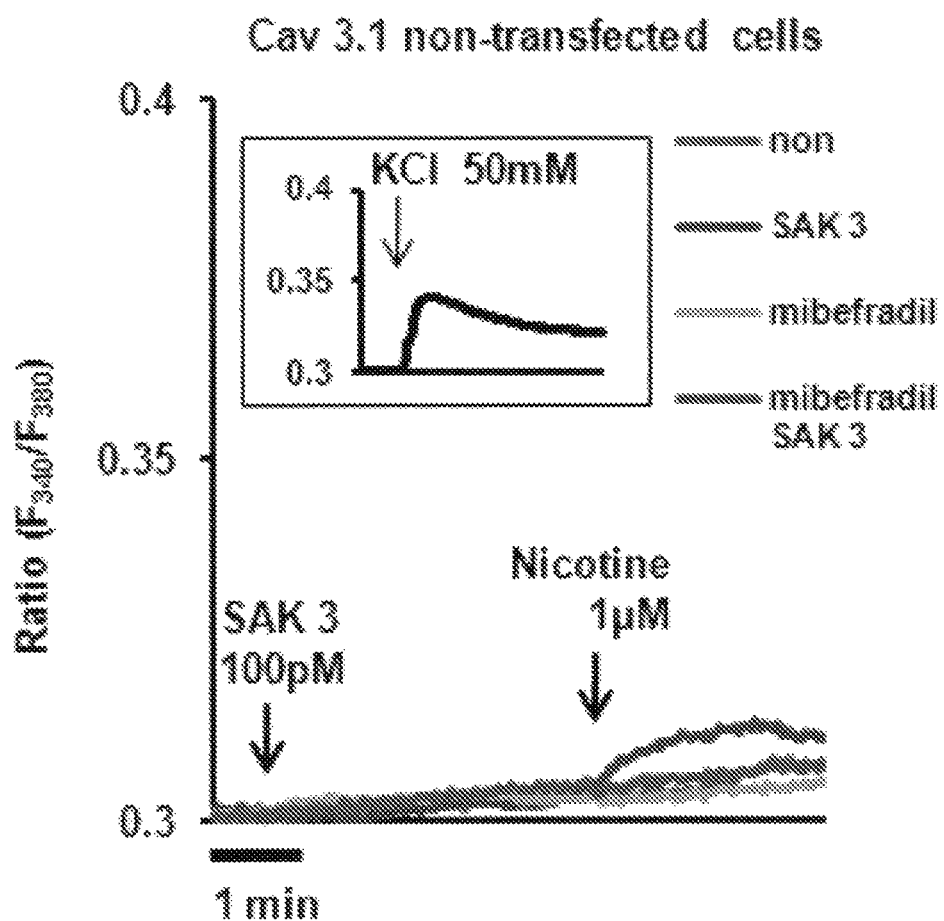
FIG. 7 is a graph showing the effect of SAK3 addition and nicotin stimulus against the level of the intercellular calcium ion in cells of non-transfected mouse neuroblastoma cell line Neuro2A. The vertical axis of the graph shows the change in the concentration of intracellular calcium ion measured by the fluorescent microscope, and the horizontal axis shows the elapsed time. Further, the change in the intracellular calcium concentration by high potassium (depolarization) stimulus is shown alongside in an inset to indicate the level of the change in the calcium concentration.
Figure 8:
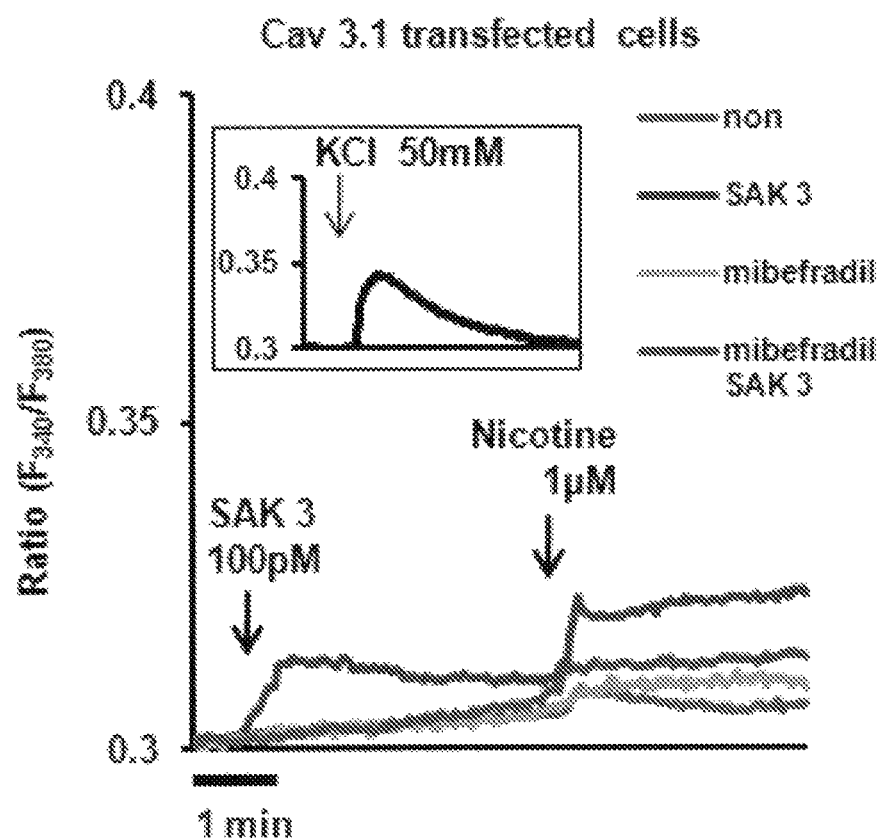
FIG. 8 is a graph showing the effect of SAK3 addition and nicotin stimulus against the level of intracellular calcium ion in the cells of the T-type calcium channel (Cav 3.1) gene-transfected mouse neuroblastoma cell line Neuro2A. The vertical axis of the graph shows the change in the concentration of intracellular calcium ion measured by the fluorescent microscope, and the horizontal axis shows the elapsed time.

The calcium concentration change over time is shown in FIG. 7 and FIG. 8. In a Cav3.1 non-expressing cell (FIG. 7), there was no change in the calcium concentration after SAK3 was added, and an increase in the calcium concentration after adding nicotin was confirmed. An increase in calcium concentration was confirmed in Cav3.1 expressing cells (FIG. 8) after SAK3 was added, but no increase in calcium concentration by SAK3 was confirmed in a system in which mibefradil was added.

Figure 9:
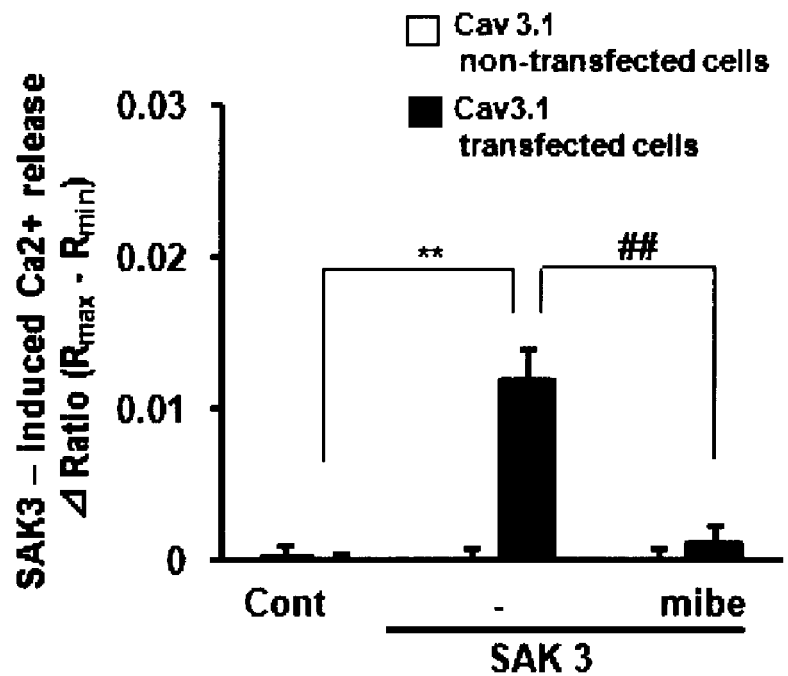
FIG. 9 is a graph showing the amount of intracellular influent calcium ion, and the white bar graph shows the result for the cells of non-transfected mouse neuroblastoma cell line Neuro2A, and the black bar shows the result for the cells of the T-type calcium channel (Cav 3.1) gene-transfected mouse neuroblastoma cell line Neuro2A. Further, "mibe" indicates that mibefradil was added. The vertical axis shows the rate of change of the change in calcium concentration (Ratio) by the SAK3 addition (Δ value) (the value obtained by subtracting the minimum value before addition from the maximum value after addition in FIG. 7). The ** in the chart shows the significance ($p<0.01$) between the control and the SAK3 treatment in the transfected cells, and ## shows the significance ($p<0.01$) between the SAK3 treatment in the transfected cell and the SAK3 treatment under the presence of mibefradil.
Figure 10:
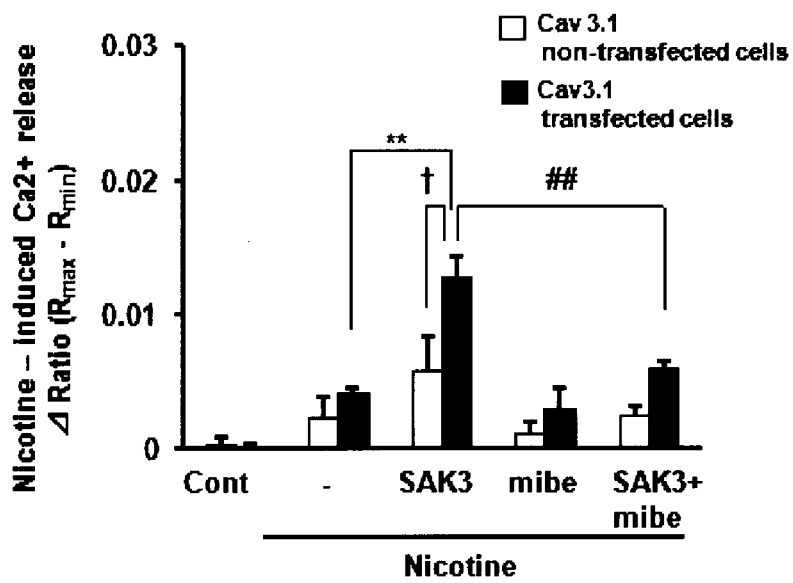
FIG. 10 is a graph showing the amount of intracellular influent calcium ion, and the white bar graph shows the result for the cells of non-transfected mouse neuroblastoma cell line Neuro2A, and the black bar shows the result for the cells of T-type calcium channel (Cav 3.1) gene-transfected mouse neuroblastoma cell line Neuro2A. Further, "mibe" indicates that mibefradil was added. The vertical axis shows the rate of change of the change in calcium concentration (Ratio) by the SAK3 addition (Δ value) (the value obtained by subtracting the minimum value before addition from the maximum value after addition in Figure in FIG. 8). The ** in the chart shows the significance ($p<0.01$) between a case when SAK3 is present and a case when it is absent, and ## shows the significance ($p<0.01$) of a case when mibefradil is present and a case when it is absent under the presence of SAK3, and + shows the significance ($p<0.05$) between non-transfected cells and transfected cells.

FIG. 9 shows the amount of intracellular influent calcium ion induced by SAK3. The Cav3.1 non-transfected cells do not show the change in the amount of influent calcium ion for SAK3, but the Cav3.1 transfected cells showed an increase in the amount of influent calcium ion. The increase was nearly cancelled out by an addition of mibefradil (mibe), which is a T type voltage-dependent calcium channel inhibitor. FIG. 10 shows an amount of influent calcium ion induced by nicotin. The increase of the amount of influent calcium ion induced by nicotin under the presence of SAK3 in transfected cells were 2 folds that of non-transfected cells. Meanwhile, the effect of SAK3 was cancelled out by adding mibefradil (mibe).

Figure 11:
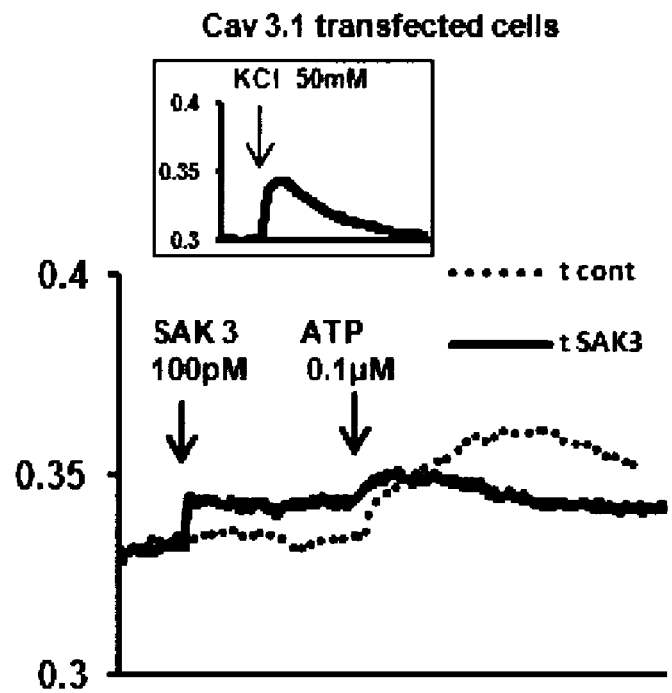
FIG. 11 is a graph showing the effect of SAK3 addition concerning a variance in the level of the intracellular ion in the cells of the T-type calcium channel (Cav 3.1) gene-transfected mouse neuroblastoma cell line Neuro2A by ATP addition. The vertical axis of the graph shows the change in the concentration of intracellular calcium ion measured by the fluorescent microscope, and the horizontal axis shows the elapsed time.
Figure 12:
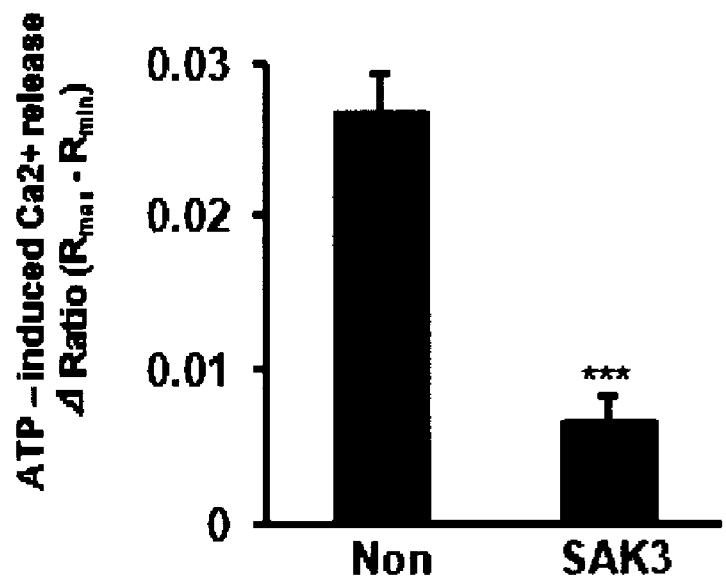
FIG. 12 is a graph showing the amount of intracellular influent calcium ion after ATP stimulus in the cells of the T-type calcium channel (Cav 3.1) gene-transfected mouse neuroblastoma cell line Neuro2A. *** in the drawing shows the significance ($p<0.001$) between a case where SAK3 is absent (Non) and a case where SAK3 is present (SAK3).
Figure 13:
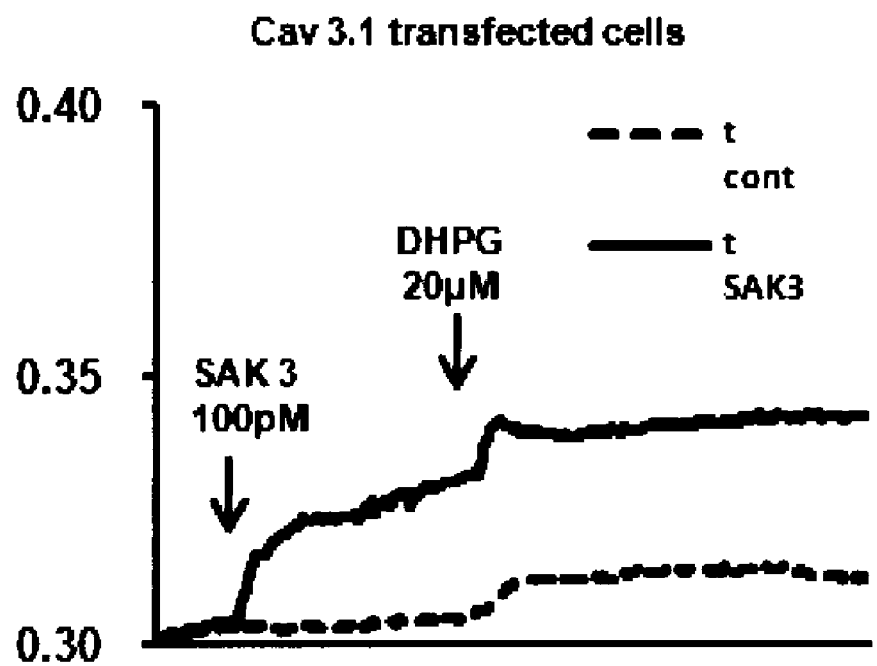
FIG. 13 is a graph showing the effect of SAK3 addition concerning the variance in the level of the intracellular ion in the cells of the T-type calcium channel (Cav 3.1) gene-transfected mouse neuroblastoma cell line Neuro2A by an addition of metabotropic glutamate receptor agonist (DHPG). The vertical axis of the graph shows the concentration of intracellular calcium ion measured by the fluorescent microscope, and the horizontal axis shows the elapsed time.
Figure 14:
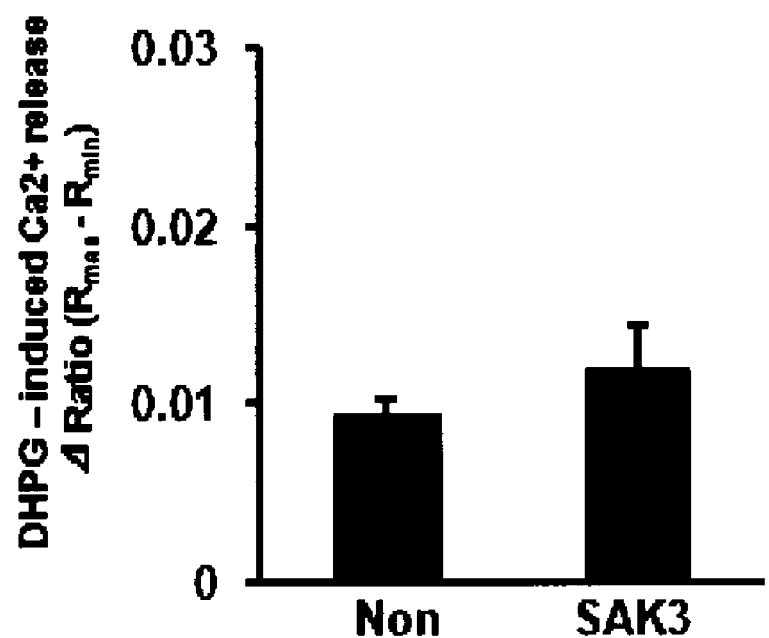
FIG. 14 is a graph showing the amount of intracellular influent calcium ion after DHPG stimulus in the cells of the T-type calcium channel (Cav 3.1) gene-transfected mouse neuroblastoma cell line Neuro2A.

FIGS. 11 to 14 show the effect of SAK3 against the ATP induction and the metabolic glutamate receptor agonist induction in a T-type calcium channel transfected cells. FIG. 11 shows the change over time of a calcium ion concentration, and FIG. 12 shows an amount of influent calcium ion induced by ATP addition. FIG. 13 shows a change over time of the calcium ion concentratin, and FIG. 14 shows an amount of influent calcium ion induced by adding 3,5-dihydroxyphenylglycin (DHPG), which is a metabolic glutamate receptor agonist. It is shown that an amount of influent calcium ion induced by adding ATP or DHPG is not potentiated under the presence of SAK3, and SAK3 does not affect an amount of influent calcium through the ATP receptor and the metabolic glutamate receptor.

Figure 15:
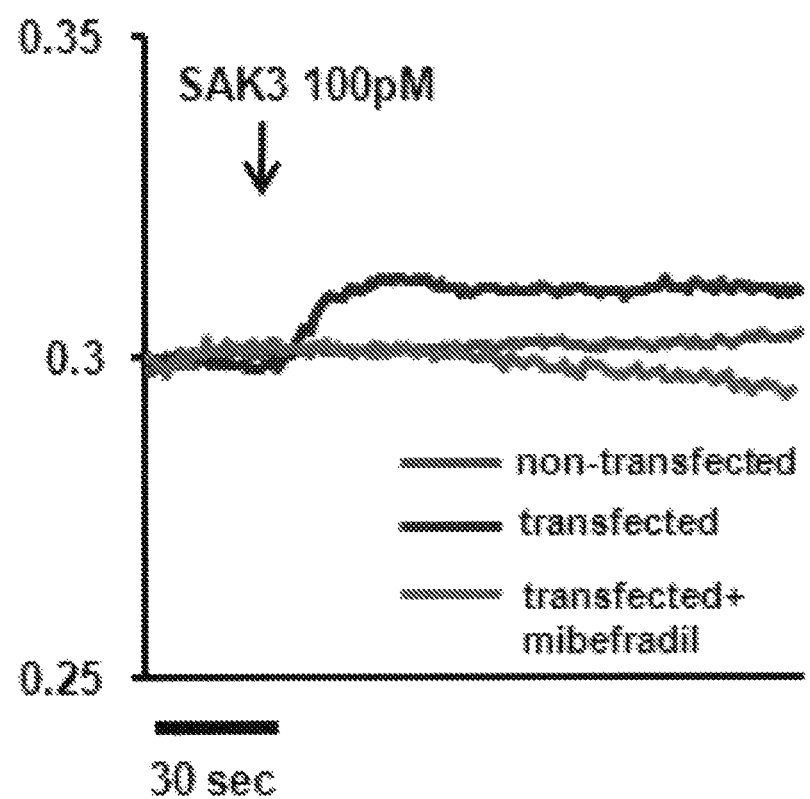
FIG. 15 is a graph showing the effect of SAK3 addition in the level of the intracellular ion in the cells of the T-type calcium channel (Cav 3.1) gene-transfected mouse neuroblastoma cell line Neuro2A. The vertical axis of the graph shows the change in the concentration of intracellular calcium ion measured by the fluorescent microscope, and the horizontal axis shows the elapsed time.
Figure 16:
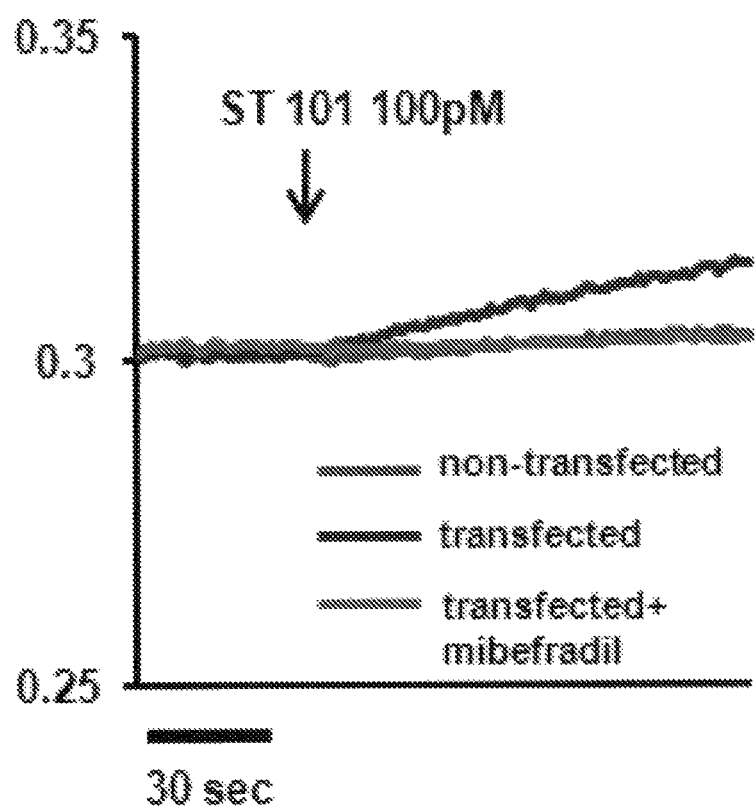
FIG. 16 is a graph showing the effect of ST101 addition in the level of the intracellular ion of the cells of the T-type calcium channel (Cav 3.1) gene-transfected mouse neuroblastoma cell line Neuro2A. The vertical axis of the graph shows the change in the concentration of intracellular calcium ion measured by the fluorescent microscope, and the horizontal axis shows the elapsed time.

Concerning the comparative test result of the effects of SAK3 and ST101 in T-type calcium channel non-transfected cells and transfected cells, FIG. 15 shows the change over time of an effect from SAK3 addition and FIG. 16 shows the change over time from adding ST101. In a T-type voltage dependent calcium channel, SAK3 shows activation that is 10 folds or higher that of ST101. The result is correlated with the difference in the CaMKII activation effect in the hippocampus nerve cell. In other words, SAK3 potentiates LTP through an activation reaction of the T-type voltage-dependent calcium channel in hippocampus nerve cells as well.

Test Example 4

Effect of Improving Cognitive Function

A 10 weeks old DDY male mouse (Nippon SLC, Hamamatsu, Japan) was used in the experiment. The animal was bred in an animal experiment facility in the Pharmaceutical Research Department of the Tohoku University Graduate School under a certain condition (temperature 22±2° C., 12 h: 12 h light-dark cycle) by freely providing water and a feed. Note that the handling of animals and animal experiments in the present paper was performed with an approval of Tohoku University Experimental Animal Committee and under the Tohoku University Animal Experiment Guideline.

An olfactolectomy mouse (OBX mouse) was prepared using a DDY male mouse. The olfactolectomy operation was performed under the condition of anesthesia by pentobarbital sodium (50 mg/kg i.p.; Dainippon, Osaka, Japan). The mouse was fixed to a brain brace, and the skull bone above the olfactory bulb was drilled to open a hole of 1 mm diameter. The olfactory bulb was sucked out with a suction pump taking care not to harm the prefrontal cortex. The same operation as the OBX group was performed for the Sham group, except for the removal of olfactory bulb by suction.

SAK3 was used by dissolving it in 5% dimethyl sulfoxide (DMSO). Thirty minutes before starting the behavioral pharmacological test, SAK3 (0.1-3.0 mg/kg) was administered into the abdominal, and the same amount of solvent (Veh.) were administered to the mice in the control group.

Y maze test: A Y maze test was performed to assess the spontaneous action amount and the spatial activity memory of a mouse. The mouse was place at the end of one of the arms in the Y maze and allowed to freely explore the maze for 8 minutes, then the positions of the arms that the mouse travelled were recorded in the order of selection. The number of times that the mouse travelled to each arm in the time of measurement was counted as total arm entries. Further, the combinations of consecutively selecting 3 different arms were counted as No. of alternation. The percentage of the No. of alternation against a number obtained by subtracting 2 from the total arm entries is shown as alternation (%) indicating the index of the normal alternation action (correct rate of spatial activity memory). The total arm entries and alternation (%) are respectively shown in FIGS. 17 and 18.

Figure 19:
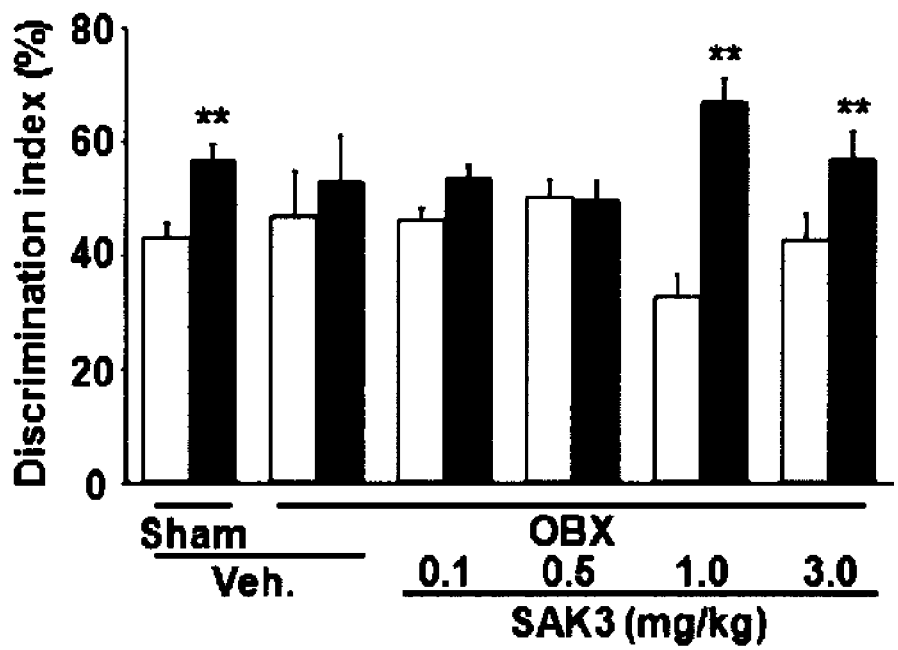
FIG. 19 is a graph showing the effect of SAK3 administration in a novel object recognition test using an olfactolectomized mouse. The percentage of the number of contacts of the known object and the novel object is shown on the vertical axis as the discrimination index. ** in the chart shows the significance ($p<0.01$) of the percentage of the number of contacts of the known object and the novel object.

Novel object recognition test: The present test uses a mouse's characteristic of preferring novel objects, and the mouse was allowed to freely explore the device in which 2 objects are placed for 10 minutes (training session). One hour after the training session, the mouse was allowed to freely explore the device in which one of the object was replaced by a novel object for 5 more minutes (trial session). The numbers of contacts for the 2 objects in the training session and the trial session were measured. The percentage (%) of the number of contacts of the novel object against the number of total contacts in the trial session was calculated as the Discrimination index. The result is shown in FIG. 19. The outline bar is the percentage of the number of total contacts in the trial session of the known object known from the training session, and the black column displays the percentage of the number of contacts of the novel object [Discrimination index].

Figure 17:
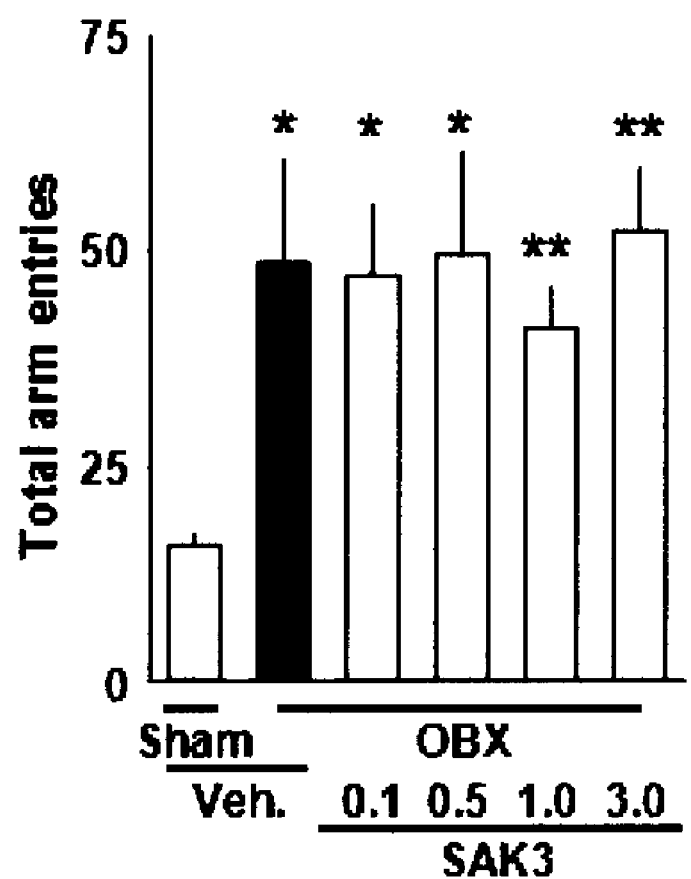
FIG. 17 is a graph showing the effect of SAK3 administration in a Y maze test using an olfactolectomized mouse. The vertical axis shows the number of times the mouse entered each arm within the measured time (total arm entries) (spontaneous movement amount). * in the chart shows the significance ($p<0.05$) with the Sham group, and ** shows the significance ($p<0.01$) with the Sham group.
Figure 18:
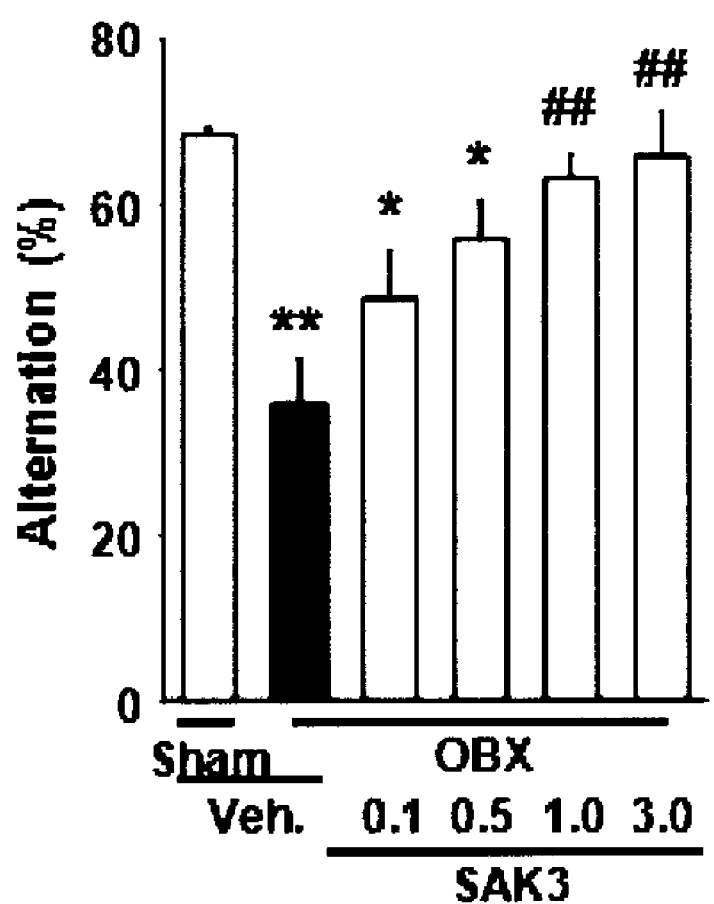
FIG. 18 is a graph showing the effect of SAK3 administration in a Y maze test using an olfactolectomized mouse. The vertical axis shows alternation (%), which is an index of a normal alternation movement (the accuracy rate of spatial activity memory). * in the chart shows the significance ($p<0.05$) with the Sham group, ** shows the significance ($p<0.01$) with the Sham group, and ## shows a significance ($p<0.05$) with the group receiving only solvent administration, that is, the OBX mouse group (Veh.+OBX).

The results of the Y maze test and the novel object cognition test in FIGS. 17 and 19 indicate that the cognitive dysfunction by olfactolectomy is almost completely improved by an administration of 1 mg/kg.

Test Example 5

Effect of Promoting Acetylcholine Liberation in Hippocampus

The amount of acetylcholine liberated in hippocampus is measured by the microdialysis method. The set up of guide cannula and dialysis probe (AG-4; Eicom, Kyoto, Japan) was conducted by fixing the mouse to the brain stereotaxis apparatus under the condition of maintaining anesthesia by 1.5% halothane (Takeda Chemical Industries Ltd., Osaka, Japan), setting up a guide cannula to the left hippocampus (AP=+3. L=+3, V=−1.8), and inserting a dialysis probe to the guide cannula. The collection of a intracerebral Ach sample from a mouse hippocampus was performed a day after the probe set up operation. After the recovery of the mouse from the operation was confirmed, the probe was connected to a micropump (ESP-64; Eicom) under an unanesthetized state and free activity, and a Ringer's solution (1.3 mM $CaCl_2$. 3 mM KCl, 146 mM NaCl and 1 mM $MgSO_4$) was introduced at a flow rate of 2 μL per minute. The dialysis sample was collected every 19.5 minutes and inserted to the acetylcholine separation column using an autoinjector (EAS-20, Eicom), and a system for a trace element analysis of biological samples (HTEC-500; Eicom) was used for analysis. SAK3 was intraperitoneally administered at 40 minutes before test (at the −40 minutes point in the graph of FIG. 8). For nicotine-induced ACh liberation, the Ringer's solution containing 3 mM nicotine was perfused from the probe for 20 minutes from the start of the test (from 0 to 20 minutes in the graph of FIG. 20), then the above Ringer's solution was replaced with a normal Ringel's solution for measurement.

Figure 20:
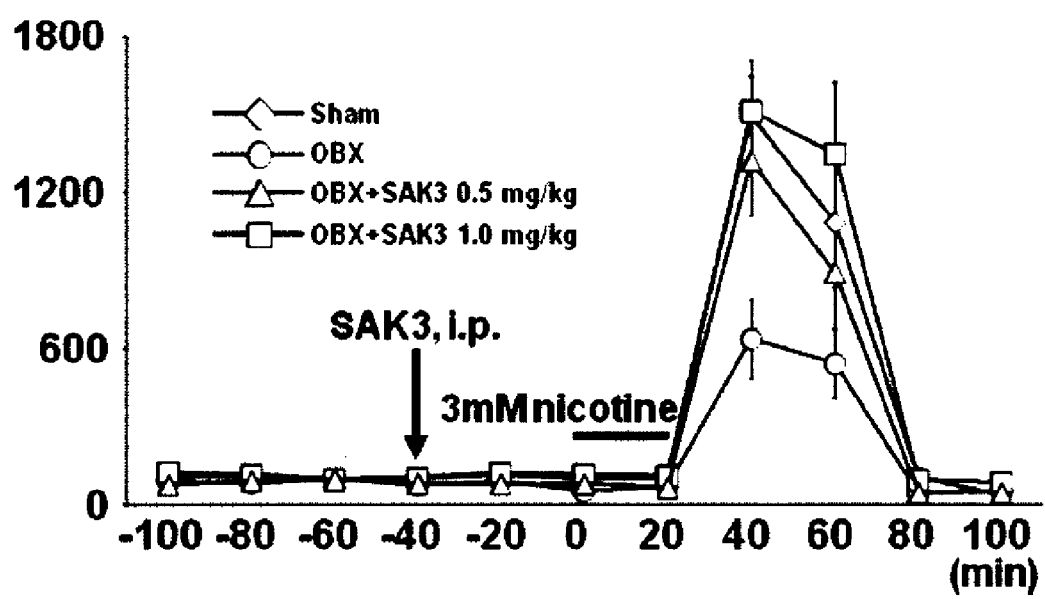
FIG. 20 is a graph showing the effect of SAK3 administration against the amount of free acetylcholine in hippocampus (quantified every 20 minutes). In the vertical axis, the amount of free acetylcholine before stimulus (−100 to −120 minutes) is set to 100%.
Figure 21:
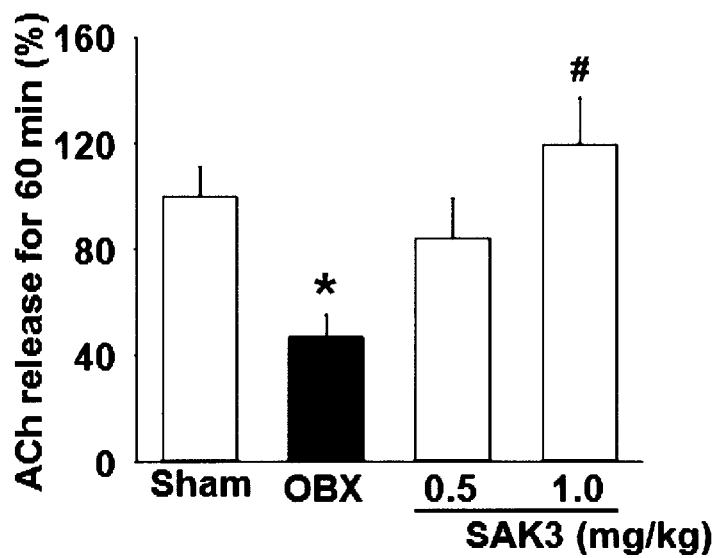
FIG. 21 is a graph showing the effect of SAK3 administration in the amount of free acetylcholine in the hippocampus of a sham operation mouse (Sham) and an olfactolectomized mouse (OBX). The vertical axis shows the amount of acetylcholine liberated between 20 to 80 minutes of elapsed time in FIG. 20 calculated by setting the Sham group as 100%. * in the graph shows the significance ($p<0.05$) between Sham and OBX, and # shows the significance ($p<0.05$) between OBX and OBX+SAK3.

The above test result is shown in FIG. 20 and FIG. 21. In an olfactolectomy mouse (OBX mouse) indicating cognitive dysfunction, the amount of acetylcholine liberated by nicotine is significantly low for the group in which SAK3 is not administered compared to the Sham group, but the amount of liberated acetylcholine increased in the SAK administration group, and the liberated amount was above that of the Sham group in a 1.0 mg/kg administration group (FIGS. 20 and 21).

Test Example 6

Effect of Self Phosphorylation Reaction (Activation Reaction) of CaMKII in the Mouse Cerebral Cortex Cell The dispersion cultivation of a mouse cerebral cortex cell was performed by a previously reported method (Fukunaga et al., J. Biol. Chem. 267, 22527-22533, 1992). After 3 weeks of cultivation, 100 pM of SAK3, SAK8, SAK9 were added to the incubation medium (KRH) for 30 minutes of incubation. The medium was removed after stimulus and the cells were frozen for preservation. The frozen cerebral cortex cells were subjected to quantification analysis of the activation state (self-phosphorylation reaction) of CaMKII by the immunoblotting method after homogenization, similarly to the method in Test Example 2.

Figure 22:
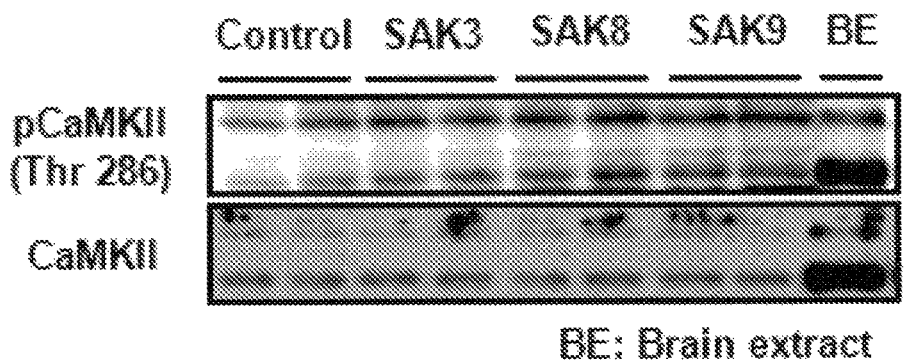
FIG. 22 is an immunoblot showing the activation reaction of CaMKII based on the index of self-phosphorylation using the cultured mouse cerebral cortex cell. It is a chart showing the result of blotting using an anti-phosphorylating CaMKII antibody and an anti-CaMKII antibody to evaluate the activation level of a mouse cerebral cortex cell when the test compounds (SAK3, SAK8 and SAK9) are added. Immunoblot was performed by subjecting BE (Brain extract) to electrophoresis to verify the electrophoresis position of protein.
Figure 23:
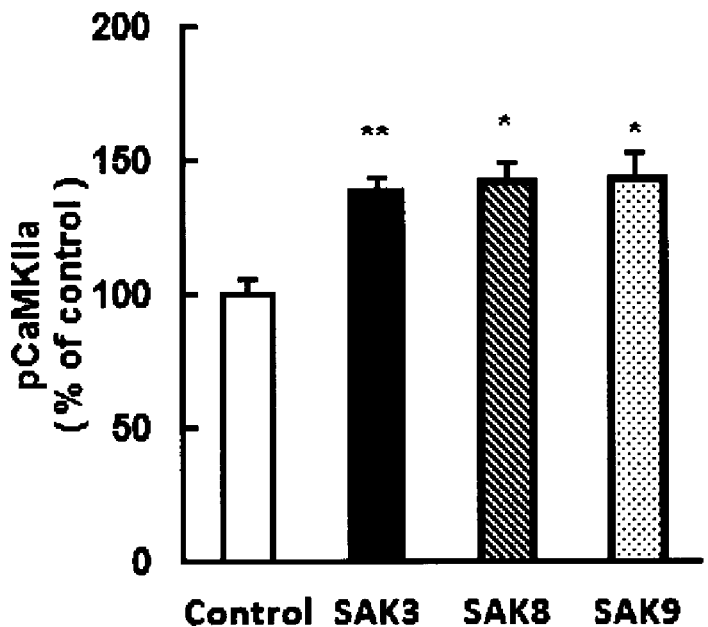
FIG. 23 is an example of a graph showing the self-phosphorylation level of CaMKII α (α subunit of 50 kDa) of a mouse cerebral cortex cell based on the quantification analysis result of the immunoreaction product from blotting. The vertical axis of the graph is a value obtained by setting the rate of phosphorylated CaMKII for the control (unstimulated) as 100%. * ($p<0.05$), ** ($p<0.01$) in the chart shows the significance between the control and the test compound.
Figure 24:
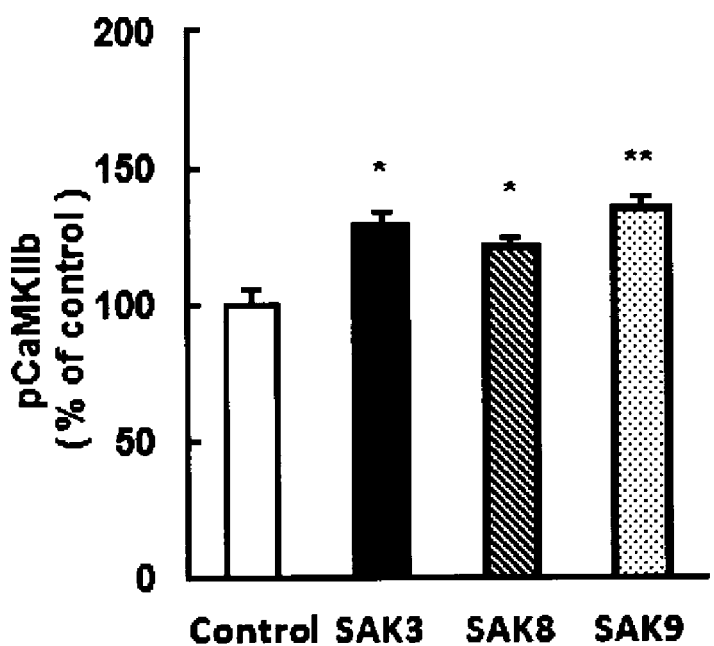
FIG. 24 is an example of a graph showing the self-phosphorylation level of CaMKII β (β subunit of 60 kDa) of a mouse cerebral cortex cell based on the quantification analysis result of the immunoreaction product from blotting. The vertical axis of the graph is a value obtained by setting the rate of phosphorylated CaMKII for the control (unstimulated) as 100%. * ($p<0.05$), ** ($p<0.01$) in the chart shows the significance between the control and the test compound.

The result of blotting using an anti-phosphorylation CaMKII antibody and an anti-CaMKII antibody is shown in FIG. 22, and the quantification analysis result of an immunoreactions product (2 examples) is shown in the graph of FIGS. 23 and 24. The mice administered SAK3, SAK8 and SAK9 have increased phosphorylated CaMKII, which demonstrates the potentiation of activation of CaMKII.

The invention claimed is:

1. A method for use in treatment of cognitive dysfunction selected from the group comprising Alzheimer's disease, Parkinson disease, Pick's disease, and Huntington's disease, schizophrenia, bipolar disorder, depression, phobia, sleep disorder, drug dependence, autism, Asperger's syndrome, mental deficiency, polyergic disorder, or tic disorder, comprising administering to a subject in need thereof an effective amount of a compound represented by formula (I):

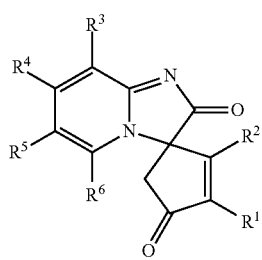

(I)

wherein, $R^1$ is a hydrogen atom, $C_{1-6}$ alkyl, cyano, —C(=O)NR$^{11}$R$^{12}$, or —C(=O)OR$^{13}$;

$R^2$ is a hydrogen atom, $C_{1-6}$ alkyl, hydroxy, —X$^1$—R$^{14}$, or —NR$^{15}$R$^{16}$;

$R^3$, $R^4$, $R^5$, and $R^6$ are each independently selected from the group consisting of a hydrogen atom, a halogen atom, $C_{1-6}$ alkyl, hydroxy, $C_{1-6}$ alkoxy, $C_{1-6}$ alkylthio, $C_{1-6}$ alkylsulfinyl, $C_{1-6}$ alkylsulfonyl, amino, $C_{1-6}$ alkylamino, di($C_{1-6}$ alkyl)amino, cyano, nitro, —C(=O)NR$^{17}$R$^{18}$, and —C(=O)OR$^{19}$;

$R^{11}$ and $R^{12}$ are each independently selected from the group consisting of a hydrogen atom, $C_{1-6}$ alkyl, $C_{6-10}$ aryl, and 5- to 10-membered heteroaryl; or $R^{11}$ and $R^{12}$, together with a nitrogen atom to which they are attached, form a nitrogen-containing heterocycle, and the nitrogen-containing heterocycle may be substituted with one or more substituents selected from the group consisting of $C_{1-6}$ alkyl, hydroxy, hydroxyC$_{1-6}$ alkyl, $C_{1-6}$ alkoxy, $C_{1-6}$ alkoxyC$_{1-6}$ alkyl, $C_{1-6}$ alkylthio, $C_{1-6}$ alkylsulfinyl, $C_{1-6}$ alkylsulfonyl, amino, $C_{1-6}$ alkylamino, di($C_{1-6}$ alkyl)amino, amino $C_{1-6}$ alkyl, ($C_{1-6}$ alkylamino)C$_{1-6}$ alkyl, [di($C_{1-6}$ alkyl)amino]C$_{1-6}$ alkyl, —C(=O)NR$^{22}$R$^{23}$, —C(=O)OR$^{24}$, —(C$_{1-6}$ alkyl)C(=O)NR$^{22}$R$^{23}$, and —(C$_{1-6}$ alkyl)C(=O)OR$^{24}$;

$R^{13}$ is selected from the group consisting of a hydrogen atom, $C_{1-6}$ alkyl, $C_{6-10}$ aryl, and 5- to 10-membered heteroaryl, wherein the alkyl group may be substituted with one or more substituents selected from the group consisting of $C_{6-10}$ aryl, hydroxy, $C_{1-6}$ alkoxy, $C_{1-6}$ alkylthio, $C_{1-6}$ alkylsulfinyl, $C_{1-6}$ alkylsulfonyl, amino, $C_{1-6}$ alkylamino, di($C_{1-6}$ alkyl)amino, —C(=O)NR$^{22}$R$^{23}$, and —C(=O)OR$^{24}$;

$X^1$ is —O—, —S—, —SO—, or —SO$_2$—;

$R^{14}$ is selected from the group consisting of $C_{1-6}$ alkyl, $C_{6-10}$ aryl, and 5- to 10-membered heteroaryl;

$R^{15}$ is hydrogen atom, $C_{1-6}$ alkyl, $C_{6-10}$ aryl, 5- to 10-membered heteroaryl, or —C(=O)—R$^{21}$, wherein the alkyl group may be substituted with one or more substituents selected from the group consisting of $C_{6-10}$ aryl, hydroxy, $C_{1-6}$ alkoxy, $C_{1-6}$ alkylthio, $C_{1-6}$ alkylsulfinyl, $C_{1-6}$ alkylsulfonyl, amino, $C_{1-6}$ alkylamino, di($C_{1-6}$ alkyl)amino, —C(=O)NR$^{22}$R$^{23}$, and —C(=O)OR$^{24}$;

$R^{16}$ is a hydrogen atom, $C_{1-6}$ alkyl, $C_{6-10}$ aryl, or 5- to 10-membered heteroaryl, wherein the alkyl group may be substituted with one or more substituents selected from the group consisting of $C_{6-10}$ aryl, hydroxy, $C_{1-6}$ alkoxy, $C_{1-6}$ alkylthio, $C_{1-6}$ alkylsulfinyl, $C_{1-6}$ alkylsulfonyl, amino, $C_{1-6}$ alkylamino, di($C_{1-6}$ alkyl)amino, —C(=O)NR$^{22}$R$^{23}$, and —C(=O)OR$^{24}$; or $R^{15}$ and $R^{16}$, together with a nitrogen atom to which they are attached, form a nitrogen-containing heterocycle, and the nitrogen-containing heterocycle may be substituted with one or more substituents selected from the group consisting of $C_{1-6}$ alkyl, hydroxy, hydroxyl $C_{1-6}$ alkyl, $C_{1-6}$ alkoxy, $C_{1-6}$ alkoxyC$_{1-6}$ alkyl, $C_{1-6}$ alkylthio, $C_{1-6}$ alkylsulfinyl, $C_{1-6}$ alkylsulfonyl, amino, $C_{1-6}$ alkylamino, di($C_{1-6}$ alkyl)amino, aminoC$_{1-6}$ alkyl, ($C_{1-6}$ alkylamino)C$_{1-6}$ alkyl, [di($C_{1-6}$ alkyl)amino]C$_{1-6}$ alkyl, —C(=O)NR$^{22}$R$^{23}$, —C(=O)OR$^{24}$, —(C$_{1-6}$ alkyl)C(=O)NR$^{22}$R$^{23}$, and —(C$_{1-6}$ alkyl)C(=O)OR$^{24}$;

$R^{17}$ and $R^{18}$ are each independently selected from the group consisting of a hydrogen atom, $C_{1-6}$ alkyl, $C_{6-10}$ aryl, and 5- to 10-membered heteroaryl; or $R^{17}$ and $R^{18}$, together with a nitrogen atom to which they are attached, form a nitrogen-containing heterocycle;

$R^{19}$ is selected from the group consisting of a hydrogen atom, $C_{1-6}$ alkyl, $C_{6-10}$ aryl, and 5- to 10-membered heteroaryl;

$R^{21}$ is selected from the group consisting of a hydrogen atom, $C_{1-6}$ alkyl, $C_{1-6}$ alkoxy, $C_{6-10}$ aryl, and 5- to 10-membered heteroaryl, wherein the alkyl group and the alkoxy group may be substituted with one or more substituents selected from the group consisting of $C_{6-10}$ aryl, hydroxy, $C_{1-6}$ alkoxy, $C_{1-6}$ alkylthio, $C_{1-6}$ alkylsulfinyl, $C_{1-6}$ alkylsulfonyl, amino, $C_{1-6}$ alkylamino, di($C_{1-6}$ alkyl)amino, —C(=O)NR$^{22}$R$^{23}$, and —C(=O)OR$^{24}$;

$R^{22}$ and $R^{23}$ are each independently selected from the group consisting of a hydrogen atom, $C_{1-6}$ alkyl, $C_{6-10}$ aryl, and 5- to 10-membered heteroaryl, or $R^{22}$ and $R^{23}$, together with a nitrogen atom to which they are attached, form a nitrogen-containing heterocycle group;

$R^{24}$ is each independently selected from the group consisting of a hydrogen atom, $C_{1-6}$ alkyl, $C_{6-10}$ aryl, and 5- to 10-membered heteroaryl, or a pharmaceutically acceptable salt thereof.

2. The method according to claim 1, wherein $R^1$ is —C(=O)OR$^{13}$, and $R^{13}$ is $C_{1-6}$ alkyl that may be substituted with one or more substituents defined in claim 1.

3. The method according to claim 1, wherein $R^2$ is $C_{1-6}$ alkylthio or —NR$^{15}$R$^{16}$, and $R^{15}$ and $R^{16}$ are as defined in claim 1.

4. The method according to claim 3, wherein group —NR$^{15}$R$^{16}$ is $C_{1-6}$ alkylamino, di($C_{1-6}$ alkyl)amino, [($C_{1-6}$ alkoxycarbonyl)$C_{1-6}$ alkyl]amino, or [($C_{6-10}$ aryl)$C_{1-6}$ alkyl] amino, or group —NR$^{15}$R$^{16}$ is a nitrogen-containing heterocyclic group selected from a 1-pyrrrolidinyl, 1-piperidinyl, 1-piperazinyl, 4-morpholinyl, or 1-homopiperidinyl, wherein the nitrogen-containing heterocyclic group may be substituted with one or more substituents selected from the group consisting of $C_{1-6}$ alkyl, hydroxy, hydroxyl $C_{1-6}$ alkyl, $C_{1-6}$ alkoxy, $C_{1-6}$ alkoxy$C_{1-6}$ alkyl, $C_{1-6}$ alkylthio, $C_{1-6}$ alkylsulfinyl, $C_{1-6}$ alkylsulfonyl, amino, $C_{1-6}$ alkylamino, di($C_{1-6}$ alkyl) amino, amino$C_{1-6}$ alkyl, ($C_{1-6}$ alkylamino)$C_{1-6}$ alkyl, [di($C_{1-6}$ alkyl)amino]$C_{1-6}$ alkyl, —C(=O)NR$^{22}$R$^{23}$, —C(=O)OR$^{24}$, —($C_{1-6}$ alkyl)C(=O)NR$^{22}$R$^{23}$, and —($C_{1-6}$ alkyl)C(=O)OR$^{24}$;

$R^{22}$ and $R^{23}$ are each independently selected from the group consisting of a hydrogen atom, $C_{1-6}$ alkyl, $C_{6-10}$ aryl, and 5- to 10-membered heteroaryl, or $R^{23}$ and $R^{23}$, together with a nitrogen atom to which they are attached, form a nitrogen-containing heterocycle group;

$R^{24}$ is each independently selected from the group consisting of a hydrogen atom, $C_{1-6}$ alkyl, $C_{6-10}$ aryl, and 5- to 10-membered heteroaryl, or a pharmaceutically acceptable salt thereof.

5. The method according to claim 1, wherein $R^3$, $R^4$, $R^5$, and $R^6$ are each independently selected from the group consisting of a hydrogen atom, and $C_{1-6}$ alkyl.

6. The method according to claim 1, wherein the compound represented by formula (I) or a pharmaceutically acceptable salt thereof is selected from the group consisting of:

2',3'-dihydro-2-methylthio-2',4-dioxospiro[2-cyclopenten-1,3'-imidazo-[1,2-a]pyridin]-3-carboxylic acid ethyl ester;

2',3'-dihydro-8-methyl-2-methylthio-2',4-dioxospiro[2-cyclopenten-1,3'-imidazo[1,2-a]pyridin]-3-carboxylic acid ethyl ester;

2',3'-dihydro-6,8-dimethyl-2-methylthio-2',4-dioxospiro[2-cyclopenten-1,3'-imidazo[1,2-a]pyridin]-3-carboxylic acid ethyl ester;

2',3'-dihydro-2-methylamino-2',4-dioxospiro[2-cyclopenten-1,3'-imidazo-[1,2-a]pyridin]-3-carboxylic acid ethyl ester;

2',3'-dihydro-8-methyl-2-methylamino-2',4-dioxospiro[2-cyclopenten-1,3'-imidazo[1,2-a]pyridin]-3-carboxylic acid ethyl ester;

2',3'-dihydro-6,8-dimethyl-2-methylamino-2',4-dioxospiro[2-cyclopenten-1,3'-imidazo[1,2-a]pyridin]-3-carboxylic acid ethyl ester;

2',3'-dihydro-2',4-dioxo-2-(phenethylamino)spiro[2-cyclopenten-1,3'-imidazo-[1,2-a]pyridin]-3-carboxylic acid ethyl ester;

2',3'-dihydro-8-methyl-2',4-dioxo-2-(phenethylamino)spiro[2-cyclopenten-1,3'-imidazo[1,2-a]pyridin]-3-carboxylic acid ethyl ester;

2',3'-dihydro-6,8-dimethyl-2',4-dioxo-2-(phenethylamino)spiro[2-cyclopenten-1,3'-imidazo[1,2-a]pyridin]-3-carboxylic acid ethyl ester;

2',3'-dihydro-2-(ethoxycarbonylmethyl)amino-2',4-dioxospiro[2-cyclopenten-1,3'-imidazo[1,2-a]pyridin]-3-carboxylic acid ethyl ester;

2',3'-dihydro-2-(ethoxycarbonylmethyl)amino-8-methyl-2',4-dioxospiro[2-cyclopenten-1,3'-imidazo[1,2-a]pyridin]-3-carboxylic acid ethyl ester;

2',3'-dihydro-2-(ethoxycarbonylmethyl)amino-6,8-dimethyl-2',4-dioxospiro[2-cyclopenten-1,3'-imidazo[1,2-a]pyridin]-3-carboxylic acid ethyl ester;

2',3'-dihydro-2-dimethylamino-2',4-dioxospiro[2-cyclopenten-1,3'-imidazo[1,2-a]pyridin]-3-carboxylic acid ethyl ester;

2',3'-dihydro-2-dimethylamino-8-methyl-2',4-dioxospiro[2-cyclopenten-1,3'-imidazo[1,2-a]pyridin]-3-carboxylic acid ethyl ester;

2',3'-dihydro-2-dimethylamino-6,8-dimethyl-2',4-dioxospiro[2-cyclopenten-1,3'-imidazo[1,2-a]pyridin]-3-carboxylic acid ethyl ester;

2',3'-dihydro-2',4-dioxo-2-piperidinospiro[2-cyclopenten-1,3'-imidazo[1,2-a]pyridin]-3-carboxylic acid ethyl ester;

2',3'-dihydro-8-methyl-2',4-dioxo-2-piperidinospiro[2-cyclopenten-1,3'-imidazo[1,2-a]pyridin]-3-carboxylic acid ethyl ester; and 2',3'-dihydro-6,8-dimethyl-2',4-dioxo-2-piperidinospiro[2-cyclopenten-1,3'-imidazo[1,2-a]pyridin]-3-carboxylic acid ethyl ester.

7. A method for activating a voltage-dependent t-type calcium channel comprising administering to a subject in need thereof an effective amount of a compound represented by formula (I):

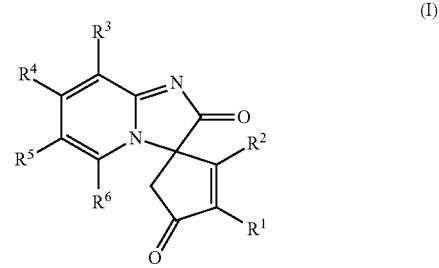

(I)

wherein, $R^1$ is a hydrogen atom, $C_{1-6}$ alkyl, cyano, —C(=O)NR$^{11}$R$^{12}$ or —C(=O)OR$^{13}$;

$R^2$ is a hydrogen atom, $C_{1-6}$ alkyl, hydroxy, —X$^1$—R$^{14}$, or —NR$^{15}$R$^{16}$;

$R^3$, $R^4$, $R^5$, and $R^6$ are each independently selected from the group consisting of a hydrogen atom, a halogen atom, $C_{1-6}$ alkyl, hydroxy, $C_{1-6}$ alkoxy, $C_{1-6}$ alkylthio, $C_{1-6}$ alkylsulfinyl, $C_{1-6}$ alkylsulfonyl, amino, $C_{1-6}$ alkylamino, di($C_{1-6}$ alkyl)amino, cyano, nitro, —C(=O)NR$^{17}$R$^{18}$, and —C(=O)OR$^{19}$;

$R^{11}$ and $R^{12}$ are each independently selected from the group consisting of a hydrogen atom, $C_{1-6}$ alkyl, $C_{6-10}$ aryl, and 5- to 10-membered heteroaryl; or $R^{11}$ and $R^{12}$, together with a nitrogen atom to which they are attached, form a nitrogen-containing heterocycle, and the nitrogen-containing heterocycle may be substituted with one or more substituents selected from the group consisting of $C_{1-6}$ alkyl, hydroxy, hydroxy$C_{1-6}$ alkyl, $C_{1-6}$ alkoxy, $C_{1-6}$ alkoxy$C_{1-6}$ alkyl, $C_{1-6}$ alkylthio, $C_{1-6}$ alkylsulfinyl, $C_{1-6}$ alkylsulfonyl, amino, $C_{1-6}$ alkylamino, di($C_{1-6}$ alkyl)amino, amino $C_{1-6}$ alkyl, ($C_{1-6}$ alkylamino)$C_{1-6}$ alkyl, [di($C_{1-6}$ alkyl)amino]$C_{1-6}$ alkyl, —C(=O)NR$^{22}$R$^{23}$, —C(=O)OR$^{24}$, —($C_{1-6}$ alkyl)C(=O)NR$^{22}$R$^{23}$, and —($C_{1-6}$ alkyl)C(=O)OR$^{24}$;

$R^{13}$ is selected from the group consisting of a hydrogen atom, $C_{1-6}$ alkyl, $C_{6-10}$ aryl, and 5- to 10-membered heteroaryl, wherein the alkyl group may be substituted with one or more substituents selected from the group consisting of $C_{6-10}$ aryl, hydroxy, $C_{1-6}$ alkoxy, $C_{1-6}$ alkylthio, $C_{1-6}$ alkylsulfinyl, $C_{1-6}$ alkylsulfonyl, amino, $C_{1-6}$ alkylamino, di($C_{1-6}$ alkyl)amino, —C(=O)NR$^{22}$R$^{23}$, and —C(=O)OR$^{24}$;

$X^1$ is —O—, —S—, —SO—, or —SO$_2$—;

$R^{14}$ is selected from the group consisting of $C_{1-6}$ alkyl, $C_{6-10}$ aryl, and 5- to 10-membered heteroaryl;

$R^{15}$ is hydrogen atom, $C_{1-6}$ alkyl, $C_{6-10}$ aryl, 5- to 10-membered heteroaryl, or —C(=O)—R$^{21}$, wherein the alkyl group may be substituted with one or more substituents selected from the group consisting of $C_{6-10}$ aryl, hydroxy, $C_{1-6}$ alkoxy, $C_{1-6}$ alkylthio, $C_{1-6}$ alkylsulfinyl, $C_{1-6}$ alkylsulfonyl, amino, $C_{1-6}$ alkylamino, di($C_{1-6}$ alkyl)amino, —C(=O)NR$^{22}$R$^{23}$, and —C(=O)OR$^{24}$;

$R^{16}$ is a hydrogen atom, $C_{1-6}$ alkyl, $C_{6-10}$ aryl, or 5- to 10-membered heteroaryl, wherein the alkyl group may be substituted with one or more substituents selected from the group consisting of $C_{6-10}$ aryl, hydroxy, $C_{1-6}$ alkoxy, $C_{1-6}$ alkylthio, $C_{1-6}$ alkylsulfinyl $C_{1-6}$ alkylsulfonyl, amino, $C_{1-6}$ alkylamino, di($C_{1-6}$ alkyl)amino, —C(=O)NR$^{22}$R$^{23}$, and —C(=O)OR$^{24}$; or $R^{15}$ and $R^{16}$, together with a nitrogen atom to which they are attached, form a nitrogen-containing heterocycle, and the nitrogen-containing heterocycle may be substituted with one or more substituents selected from the group consisting of $C_{1-6}$ alkyl, hydroxy, hydroxyl $C_{1-6}$ alkyl, $C_{1-6}$ alkoxy, $C_{1-6}$ alkoxy$C_{1-6}$ alkyl, $C_{1-6}$ alkylthio, $C_{1-6}$ alkylsulfinyl, $C_{1-6}$ alkylsulfonyl, amino, $C_{1-6}$ alkylamino, di($C_{1-6}$ alkyl)amino, amino$C_{1-6}$ alkyl, ($C_{1-6}$ alkylamino)$C_{1-6}$ alkyl, [di($C_{1-6}$ alkyl)amino]$C_{1-6}$ alkyl, —C((=O)NR$^{22}$R$^{23}$, —C(=O)OR$^{24}$, —($C_{1-6}$ alkyl)C(=O)NR$^{22}$R$^{23}$, and —($C_{1-6}$ alkyl)C(=O)OR$^{24}$;

$R^{17}$ and $R^{18}$ are each independently selected from the group consisting of a hydrogen atom, $C_{1-6}$ alkyl, $C_{6-10}$ aryl, and 5- to 10-membered heteroaryl; or $R^{17}$ and $R^{18}$, together with a nitrogen atom to which they are attached, form a nitrogen-containing heterocycle;

$R^{19}$ is selected from the group consisting of a hydrogen atom, $C_{1-6}$ alkyl, $C_{6-10}$ aryl, and 5- to 10-membered heteroaryl;

$R^{21}$ is selected from the group consisting of a hydrogen atom, $C_{1-6}$ alkyl, $C_{1-6}$ alkoxy, $C_{6-10}$ aryl, and 5- to 10-membered heteroaryl, wherein the alkyl group and the alkoxy group may be substituted with one or more substituents selected from the group consisting of $C_{6-10}$ aryl, hydroxy, $C_{1-6}$ alkoxy, $C_{1-6}$ alkylthio, $C_{1-6}$ alkylsulfinyl, $C_{1-6}$ alkylsulfonyl, amino, $C_{1-6}$ alkylamino, di($C_{1-6}$ alkyl)amino, —C(=O)NR$^{22}$R$^{23}$, and —C(=O)OR$^{24}$;

$R^{22}$ and $R^{23}$ are each independently selected from the group consisting of a hydrogen atom, $C_{1-6}$ alkyl, $C_{6-10}$ aryl, and 5- to 10-membered heteroaryl, or $R^{22}$ and $R^{23}$, together with a nitrogen atom to which they are attached, form a nitrogen-containing heterocycle group;

$R^{24}$ is each independently selected from the group consisting of a hydrogen atom, $C_{1-6}$ alkyl, $C_{6-10}$ aryl, and 5- to 10-membered heteroaryl, or a pharmaceutically acceptable salt thereof.

8. The method according to claim 7, wherein $R^1$ is —C(=O)OR$^{13}$, and $R^{13}$ is a $C_{1-6}$ alkyl that may be substituted with one or more substituents selected from the group consisting of $C_{6-10}$ aryl, hydroxy, $C_{1-6}$ alkoxy, $C_{1-6}$ alkylthio, $C_{1-6}$ alkylsulfinyl, $C_{1-6}$ alkylsulfonyl, amino, $C_{1-6}$ alkylamino, di($C_{1-6}$ alkyl)amino, —C(=O)NR$^{22}$R$^{23}$, and —C(=O)OR$^{24}$;

$R^{22}$ and $R^{23}$ are each independently selected from the group consisting of a hydrogen atom, $C_{1-6}$ alkyl, $C_{6-10}$ aryl, and 5- to 10-membered heteroaryl, or $R^{22}$ and $R^{23}$, together with a nitrogen atom to which they are attached, form a nitrogen-containing heterocycle group;

$R^{24}$ is each independently selected from the group consisting of a hydrogen atom, $C_{1-6}$ alkyl, $C_{6-10}$ aryl, and 5- to 10-membered heteroaryl, or a pharmaceutically acceptable salt thereof.

9. The method according to claim 7, wherein $R^2$ is $C_{1-6}$ alkylthio or —NR$^{15}$R$^{16}$, and $R^{15}$ and $R^{16}$ are selected from the group consisting of $C_{1-6}$ alkyl, hydroxy, hydroxyl $C_{1-6}$ alkyl, $C_{1-6}$ alkoxy, $C_{1-6}$ alkoxy$C_{1-6}$ alkyl, $C_{1-6}$ alkylthio, $C_{1-6}$ alkylsulfinyl, $C_{1-6}$ alkylsulfonyl, amino, $C_{1-6}$ alkylamino, di($C_{1-6}$ alkyl)amino, amino$C_{1-6}$ alkyl, ($C_{1-6}$ alkylamino)$C_{1-6}$ alkyl, [di($C_{1-6}$ alkyl)amino]$C_{1-6}$ alkyl, —C(=O)NR$^{22}$R$^{23}$, —C(=O)OR$^{24}$, —($C_{1-6}$ alkyl)C(=O)NR$^{22}$R$^{23}$, and —($C_{1-6}$ alkyl)C(=O)OR$^{24}$;

$R^{22}$ and $R^{23}$ are each independently selected from the group consisting of a hydrogen atom, $C_{1-6}$ alkyl, $C_{6-10}$ aryl, and 5- to 10-membered heteroaryl, or $R^{22}$ and $R^{23}$, together with a nitrogen atom to which they are attached, form a nitrogen-containing heterocycle group;

$R^{24}$ is each independently selected from the group consisting of a hydrogen atom, $C_{1-6}$ alkyl, $C_{6-10}$ aryl, and 5- to 10-membered heteroaryl, or a pharmaceutically acceptable salt thereof.

10. The method according to claim 9, wherein group —NR$^{15}$R$^{16}$ is $C_{1-6}$ alkylamino, di($C_{1-6}$ alkyl)amino, [($C_{1-6}$ alkoxycarbonyl)$C_{1-6}$ alkyl]amino, or [($C_{6-10}$ aryl)$C_{1-6}$ alkyl] amino, or group —NR$^{15}$R$^{16}$ is a nitrogen-containing heterocyclic group selected from 1-pyrrolidinyl, 1-piperidinyl, 1-piperazinyl, 4-morpholinyl, or 1-homopiperidinyl, wherein the nitrogen-containing heterocyclic group may be substituted with one or more substituents selected from the group consisting of $C_{1-6}$ alkyl, hydroxy, hydroxyl $C_{1-6}$ alkyl, $C_{1-6}$ alkoxy, $C_{1-6}$ alkoxy$C_{1-6}$ alkyl, $C_{1-6}$ alkylthio, $C_{1-6}$ alkylsulfinyl, $C_{1-6}$ alkylsulfonyl, amino, $C_{1-6}$ alkylamino, di($C_{1-6}$ alkyl)amino, amino$C_{1-6}$ alkyl, ($C_{1-6}$ alkylamino)$C_{1-6}$ alkyl, [di($C_{1-6}$ alkyl)amino]$C_{1-6}$ alkyl, —C(=O)NR$^{22}$R$^{23}$, —C(=O)OR$^{24}$, —($C_{1-6}$ alkyl)C(=O)NR$^{22}$R$^{23}$, and —($C_{1-6}$ alkyl)C(=O)OR$^{24}$;

$R^{22}$ and $R^{23}$ are each independently selected from the group consisting of a hydrogen atom, $C_{1-6}$ alkyl, $C_{6-10}$ aryl, and 5- to 10-membered heteroaryl, or $R^{22}$ and $R^{23}$, together with a nitrogen atom to which they are attached, form a nitrogen-containing heterocycle group;

$R^{24}$ is each independently selected from the group consisting of a hydrogen atom, $C_{1-6}$ alkyl, $C_{6-10}$ aryl, and 5- to 10-membered heteroaryl, or a pharmaceutically acceptable salt thereof.

11. The method according to claim 7, wherein $R^3$, $R^4$, $R^5$, and $R^6$ is each independently selected from a group consisting of a hydrogen atom; and $C_{1-6}$ alkyl.

12. The method according to claim 7, wherein the compound represented by formula (I) or a pharmaceutically acceptable salt thereof is selected the group consisting of:

2',3'-dihydro-2-methylthio-2',4-dioxospiro[2-cyclopenten-1,3'-imidazo-[1,2-a]pyridin]-3-carboxylic acid ethyl ester;

2',3'-dihydro-8-methyl-2-methylthio-2',4-dioxospiro[2-cyclopenten-1,3'-imidazo[1,2-a]pyridin]-3-carboxylic acid ethyl ester;

2',3'-dihydro-6,8-dimethyl-2-methylthio-2',4-dioxospiro[2-cyclopenten-1,3'-imidazo[1,2-a]pyridin]-3-carboxylic acid ethyl ester;

2',3'-dihydro-2-methylamino-2',4-dioxospiro[2-cyclopenten-1,3'-imidazo-[1,2-a]pyridin]-3-carboxylic acid ethyl ester;

2',3'-dihydro-8-methyl-2-methylamino-2',4-dioxospiro[2-cyclopenten-1,3'-imidazo[1,2-a]pyridin]-3-carboxylic acid ethyl ester;

2',3'-dihydro-6,8-dimethyl-2-methylamino-2',4-dioxospiro[2-cyclopenten-1,3'-imidazo[1,2-a]pyridin]-3-carboxylic acid ethyl ester;

2',3'-dihydro-2',4-dioxo-2-(phenethylamino)spiro[2-cyclopenten-1,3'-imidazo-[1,2-a]pyridin]-3-carboxylic acid ethyl ester;

2',3'-dihydro-8-methyl-2',4-dioxo-2-(phenethylamino)spiro[2-cyclopenten-1,3'-imidazo[1,2-a]pyridin]-3-carboxylic acid ethyl ester;

2',3'-dihydro-6,8-dimethyl-2',4-dioxo-2-(phenethylamino)spiro[2-cyclopenten-1,3'-imidazo[1,2-a]pyridin]-3-carboxylic acid ethyl ester;

2',3'-dihydro-2-(ethoxycarbonylmethyl)amino-2',4-dioxospiro[2-cyclopenten-1,3'-imidazo[1,2-a]pyridin]-3-carboxylic acid ethyl ester;

2',3'-dihydro-2-(ethoxycarbonylmethyl)amino-8-methyl-2',4-dioxospiro[2-cyclopenten-1,3'-imidazo[1,2-a]pyridin]-3-carboxylic acid ethyl ester;

2',3'-dihydro-2-(ethoxycarbonylmethyl)amino-6,8-dimethyl-2',4-dioxospiro[2-cyclopenten-1,3'-imidazo[1,2-a]pyridin]-3-carboxylic acid ethyl ester;

2',3'-dihydro-2-dimethylamino-2',4-dioxospiro[2-cyclopenten-1,3'-imidazo[1,2-a]pyridin]-3-carboxylic acid ethyl ester;

2',3'-dihydro-2-dimethylamino-8-methyl-2',4-dioxospiro[2-cyclopenten-1,3'-imidazo[1,2-a]pyridin]-3-carboxylic acid ethyl ester;

2',3'-dihydro-2-dimethylamino-6,8-dimethyl-2',4-dioxospiro[2-cyclopenten-1,3'-imidazo[1,2-a]pyridin]-3-carboxylic acid ethyl ester;

2',3'-dihydro-2',4-dioxo-2-piperidinospiro[2-cyclopenten-1,3'-imidazo[1,2-a]pyridin]-3-carboxylic acid ethyl ester;

2',3'-dihydro-8-methyl-2',4-dioxo-2-piperidinospiro[2-cyclopenten-1,3'-imidazo[1,2-a]pyridin]-3-carboxylic acid ethyl ester; and 2',3'-dihydro-6,8-dimethyl-2',4-dioxo-2-piperidinospiro[2-cyclopenten-1,3'-imidazo[1,2-a]pyridin]-3-carboxylic acid ethyl ester.

\* \* \* \* \*